(12) United States Patent
Buvat et al.

(10) Patent No.: US 9,196,847 B2
(45) Date of Patent: Nov. 24, 2015

(54) SENSITIZING COMPLEXES, PROCESS FOR THE PREPARATION THEREOF, SEMICONDUCTIVE INORGANIC/ORGANIC HYBRID MATERIAL COMPRISING THEM, AND PHOTOVOLTAIC CELL COMPRISING SAID MATERIAL

(75) Inventors: Pierrick Buvat, Montbazon (FR); Fabrice Odobel, Nantes (FR); Coralie Houarner, Nantes (FR); Errol Blart, Grandchamp des Fontaines (FR)

(73) Assignee: COMMISSARIAT A L'ENERGIE ATOMIQUE, Paris (FR)

( * ) Notice: Subject to any disclaimer, the term of this patent is extended or adjusted under 35 U.S.C. 154(b) by 1517 days.

(21) Appl. No.: 12/158,281

(22) PCT Filed: Dec. 22, 2006

(86) PCT No.: PCT/EP2006/070189
§ 371 (c)(1),
(2), (4) Date: Jun. 19, 2008

(87) PCT Pub. No.: WO2007/071792
PCT Pub. Date: Jun. 28, 2007

(65) Prior Publication Data
US 2008/0276985 A1    Nov. 13, 2008

(30) Foreign Application Priority Data

Dec. 23, 2005 (FR) ...................................... 05 13259

(51) Int. Cl.
*C08C 19/22* (2006.01)
*C08C 19/24* (2006.01)
*C08F 8/00* (2006.01)
*H01L 51/00* (2006.01)
*C07D 213/53* (2006.01)
*C07F 15/00* (2006.01)
*H01L 51/42* (2006.01)

(52) U.S. Cl.
CPC .......... *H01L 51/0086* (2013.01); *C07D 213/53* (2013.01); *C07F 15/0053* (2013.01); *H01L 51/0068* (2013.01); *H01L 51/4226* (2013.01); *H01L 51/0035* (2013.01); *H01L 51/0036* (2013.01); *Y02E 10/549* (2013.01)

(58) Field of Classification Search
USPC ................ 525/340, 328.5, 375, 360; 136/263
See application file for complete search history.

(56) References Cited

U.S. PATENT DOCUMENTS

| | | |
|---|---|---|
| 5,441,827 A | 8/1995 | Gratzel et al. |
| 6,512,172 B1 | 1/2003 | Salafsky et al. |
| 2002/0017656 A1 | 2/2002 | Graetzel et al. |
| 2007/0066778 A1 | 3/2007 | Belleville et al. |

FOREIGN PATENT DOCUMENTS

| | | |
|---|---|---|
| EP | 0917208 A1 | 5/1999 |
| EP | 1176646 A1 | 1/2002 |
| FR | 2862429 A1 | 5/2005 |
| JP | 07-500630 A | 1/1995 |
| JP | 2000-106223 A | 4/2000 |
| JP | 2003-272721 A | 9/2003 |
| JP | 2006-517543 A | 7/2006 |
| WO | 93/19479 A1 | 9/1993 |
| WO | 93/20569 A1 | 10/1993 |
| WO | 94/14440 A1 | 7/1994 |
| WO | 2004/067533 A1 | 8/2004 |
| WO | 2005/050752 A1 | 6/2005 |

OTHER PUBLICATIONS

Krebs et al., Solar Energy Materials & Solar Cells, 90, 142-165 (2006).*
Krebs et al., "Dye Sensitized Photovoltaic Cells: Attaching Conjugated Polymers to Zwitterionic Ruthenium Dyes," Solar Energy Materials & Solar Cells, 90, 142-165 (2006).*
Bach et al., "Charge Separation in Solid-State Dye-Sensitized Heterojunction Solar Cells," J. Am. Chem. Soc. 121 (32):7445-6 (1999).
Bach et al., "Solid-State Dye-Sensitized Mesoporous TiO2 Solar Cells with High Photon-to-electron Conversion Efficiencies," Nature 395:583-5 (1998).
Bixon et al., "Electron Transfer—From Isolated Molecules to Biomelecules," School of Chemistry, Tel Aviv University, Ramat Aviv, Tel Aviv, Israel pp. 35-202 (1999).
Duffy et al., "Investigation of the Kinetics of the Back Reaction of Electrons with Tri-Iodide in Dye-Sensitized Nanocrystalline Photovoltaic Cells," J. Phys. Chem. 104(38):8916-9 (2000).

(Continued)

*Primary Examiner* — Monique Peets
(74) *Attorney, Agent, or Firm* — Nixon Peabody LLP

(57) ABSTRACT

Complex of formula (I)

in which:

F represents one or more groups capable of grafting chemically to a substrate of semiconductive porous oxide ceramic;

S represents a sensitizing group for sensitizing a semiconductive porous oxide ceramic;

C is a conductive polymer;

E is a deconjugating spacer group which makes it possible to electrically isolate the sensitizer (S) from the electron-conductive polymer (C).

24 Claims, 1 Drawing Sheet

(56) References Cited

OTHER PUBLICATIONS

Gebeyehu et al., "Hybrid Solar Cells on Dye-Sensitized Nanoporous TiO2 Electrodes and Conjugated Polymers as Hole Transport Materials," Synthetic Metals 125:279-87 (2002).
Gebeyehu et al., "Solid State Dye-Sensitized TiO2 Solar Cells with Poly(3-octylthiophene) as Hole Transport Layer," Synthetic Metals 121:1549-50 (2001).
Gebeyehu et al., "Solid-State Organic/Inorganic Hybrid Solar Cells Based on Conjugated Polymers and Dye-Sensitized TiO2 Electrodes," Thin Solid Films 403-404:271-4 (2002).
Hagfeldt et al., "Light-Induced Redox Reactions in Nanocrystalline Systems," Chem. Rev. 95(1):49-68 (1995).
Hao et al., "A Photoelectrochemical Solar Cell Based on ZnO/dye/Polypyrrole Film Electrode as Photoanode," Solar Energy Materials & Solar Cells 60:349-59 (2000).
Haridas et al., "Synthesis of Low Melting Hole Conductor Systems Based on Triarylamines and Application in Dye Sensitized Solar Cells," Synthetic Metals 121:1573-4 (2001).
Jäger et al., "Hybrid Solar Cells with Novel Hole Transporting Poly(triphenyldiamine)s," Synthetic Metals 121:1543-4 (2001).
Jeffries-El et al., "In-Situ End-Group Functionalization of Regioregular Poly(3-alkylthiophene) Using the Grignard Metathesis Polymerization Method," Adv. Mater. 16(12):1017-9 (2004).
Jortner et al., "A 'Chemistry for the 21st Century' Monograph," Molecular Electronics (1997).
Kajihara et al., "Photovoltaic Effect in Titanium Dioxide/Polythiophene Cell," J. Appl. Phys. 36(Pt.1, No. 9A):5537-42 (1997).
Kalyanasundaram et al., "Applications of Functionalized Transition Metal Complexes in Photonic and Optoelectronic Devices," Coordination Chemistry Reviews 177:347-414 (1998).
Kaneko et al., "Photovoltaic Cell Using High Mobility Poly(alkylthiophene)s and TiO2," Synthetic Metals 121:1537-8 (2001).
Kinoshita et al., "Creation of Novel Light Sensitive Amorphous Molecular Materials and Their Photovoltaic Properties," Synthetic Metals 121:1571-2 (2001).
Krebs et al., "Dye Sensitized Photovoltaic Cells: Attaching Conjugated Polymers to Zwitterionic Ruthenium Dyes," Solar Energy Materials & Solar Cells 90:142-65 (2006).
Kumara et al., "Dye-Sensitized Solar Cell with the Hole Collector p-CuSCN Deposited fro9m a Solution in npropylsuphide," Solar Energy Materials & Solar Cells 69:195-9 (2001).
Murakoshi et al., "Fabrication of Solid-State Dye-Sensitized TiO2 Solar Cells Combined with Polypyrrole," Solar Energy Materials and Solar Cells 55:113-25 (1998).
Murakoshi et al., "Solid State Dye-Sensitized TiO2 Solar Cell with Polypyrrole as Hole Transport Layer," Chemistry Letters the Chemical Society of Japan pp. 471-472 (1997).
Nagamatsu et al., "Photocarrier Transport in Processable Poly(3-alkylthiophene)," Synthetic Metals 121:1563-4 (2001).
Nogueira et al., Polymers in Dye Sensitized Solar Cells: Overview and Perspectives, Coordination Chemistry Reviews 248:1455-68 (2004).
Odobel et al., "Preparations and Characterizations of Bichromophoric Systems Composed of a Ruthenium Polypyridine Complex Connected to a Difluoroborazaindacene or a Zinc Phthalocyanine Chromophore," Inorganic Chemistry 44(16):5600-11 (2005).
O'Regan et al., "A Low-Cost, High-Efficiency Solar Cell Based on Dye-Sensitized Colloidal TiO2 Films," Nature 353:737-40 (1991).
O'Regan et al., "Large Enhancement in Photocurrent Efficiency Caused by UV Illumination of the Dye-Sensitized Heterojunction TiO2/RuLL'NCS/CuSCN: Initiation and Potential Mechanisms," Chem. Mater. 10(6):1501-9 (1998).
Perera et al., "Recombination Process in Dye-Sensitized Solid-State Solar Cells with CuI as the Hole Collector," Solar Energy Materials & Solar Cells 79:249-55 (2003).
Saito et al., "Photo-Sensitizing Ruthenium Complexes for Solid State Dye Solar Cells in Combination with Conducting Polymers as Hole Conductors," Coordination Chemistry reviews 248:1469-78 (2004).
Senadeera et al, "Fabrication of Highly Efficient Polythiophene-Sensitized Metal Oxide Photovoltaic Cells," Applied Physics Letters 83(26):5470-2 (2003).
Spiekermann et al., "Poly(4-undecyl-2,2'-bithiophene) as a Hole Conductor in Solid State Dye Sensitized Titanium Dioxide Solar Cells," Synthetic Metals 121:1603-4 (2001).
Takayama et al., "Photocarrier Generation in Regioregular Poly(3-alkylthiophene) Photovoltaic Cells," Synthetic Metals 121:1565-6 (2001).
Houarner, C., et al., "Ruthenium bis-terpyridine complexes connected to an oligothiophene unit for dry dye-sensitised solar cells," Photochemical and Photobiological Sciences, Feb. 2005, 4(2):200-4. Epub Dec. 2004.
Kanato, H., et al., "Synthesis and Photophysical Properties of Ferrocene-Oligothiophene-Fullerene Triads," Journal of Organic Chemistry, Oct. 2004, 69(21):7183-9.
Galoppini, E., "Linkers for anchoring sensitizers to semiconductor nanoparticles," Coordination Chemistry Reviews, Elsevier Science, vol. 248, No. 13-14, Jul. 2004, pp. 1283-1297.
Kimura, M., et al., "Synthesis of Multicomponent Systems Composed of One Phthalocyanine and Four Terpyridine Ligands," Inorganic Chemistry, 40(18), Jul. 2001, pp. 4775-4779.

\* cited by examiner

SENSITIZING COMPLEXES, PROCESS FOR THE PREPARATION THEREOF, SEMICONDUCTIVE INORGANIC/ORGANIC HYBRID MATERIAL COMPRISING THEM, AND PHOTOVOLTAIC CELL COMPRISING SAID MATERIAL

CROSS REFERENCE TO RELATED APPLICATIONS OR PRIORITY CLAIM

This application is a national phase of International Application No. PCT/EP2006/070189, entitled "SENSITIZING COMPLEXES, PROCESS FOR THE PREPARATION THEREOF, SEMICONDUCTIVE INORGANIC/ORGANIC HYBRID MATERIAL COMPRISING THEM, AND PHOTOVOLTAIC CELL COMPRISING SAID MATERIAL", which was filed on Dec. 22, 2006, and which claims priority of French Patent Application No. 05 13259, filed Dec. 23, 2005.

DESCRIPTION

1. Technical Field

The present invention relates to novel sensitizing complexes, dyes, intended to be used in photoelectrochemical cells, and more particularly in photovoltaic cells.

The present invention also relates to a process for preparing these novel sensitizing complexes, dyes.

The present invention also relates to a pn-semiconductive (semiconductor) inorganic/organic hybrid material comprising said sensitizing complexes, dyes, and a substrate of porous oxide ceramic such as $TiO_2$.

The present invention also relates to a process for preparing said inorganic/organic hybrid material.

Finally, the invention relates to a photovoltaic cell comprising said inorganic/organic hybrid material.

The technical field of the invention can be defined in general as that of photoelectrochemical cells, more particularly of photovoltaic cells, or else of light-emitting diodes.

2. Prior Art

A photovoltaic cell is a device for converting photochemical energy to electrical energy.

In general, a photovoltaic cell is made up of p-doped semiconductive (semiconductor) materials (i.e. those having a deficiency of electrons, i.e. charge holes) and of n-doped semiconductive (semiconductor) materials (i.e. those having an excess of electrons), joined together to form a junction called a "pn junction", which provides separation between the electrons and the charge holes. This separation generates a potential difference at the pn junction and consequently an electric current if a contact is placed on the n-region and a contact is placed on the p-region and a resistor (namely a device intended to be supplied with electric current) is placed between these two contacts.

Thus, when light strikes the region of the cell consisting of the junction between the p-type semiconductive (semiconductor) material and the n-type semiconductive (semiconductor) material, the constituent photons of the light are absorbed by said region and each absorbed photon creates an electron and a hole (referred to as an electron-hole pair), said pair being separated at the junction between the n-type material and the p-type material, thus creating a potential difference on either side of this junction.

Until recently, most photovoltaic cells have been produced from silicon, more specifically silicon doped with atoms such as phosphorus in order to form the n-region and silicon doped with atoms such as boron in order to form the p-region of the cell. However, the use of silicon proves to be expensive.

To remedy this drawback, research has endeavoured to develop new materials that can be used to construct photovoltaic cells.

Thus, photovoltaic cells have been designed from a pn-type semiconductive (semiconductor) material comprising a solid n-semiconductive (semiconductor) region and a liquid p-semiconductive (semiconductor) region. More specifically, the n-semiconductive region consists of a porous oxide ceramic, for example titanium dioxide, the pores of which are filled with a charge-conducting liquid electrolyte, this electrolyte fulfilling the role of p-semiconductive region, by analogy with conventional photovoltaic cells.

This type of photovoltaic cell, the principle of which is therefore based essentially on the sensitization of thin nanocrystalline layers of titanium oxide, makes it possible to achieve photoconversion efficiencies of the order of 10% using sensitizers based on polypyridine ruthenium complexes [1], [2], [3].

This type of photovoltaic cell is in particular described in international patent application WO-A-93/19479.

However, it has been noted that photovoltaic cells that use a liquid electrolyte have the following drawbacks:

low stability over time, owing to the evaporation of the solvents used in the composition of the electrolyte;

relatively limited operating temperature range because of the volatile nature of the solvents used in the formation of the electrolyte;

risk of precipitating the salts used in forming the electrolyte, when the photovoltaic cell is made to operate at very low temperatures, such as temperatures of the order of −10° C. to −40° C.; and restricting implementation owing to the use of a liquid electrolyte, excluding in particular the use of flexible organic supports and/or those of large dimensions.

In other words, the wide-scale industrial development of these liquid-electrolyte photovoltaic cells comes up against a major technological problem caused by the liquid electrolyte contained by the cell. In fact, the liquid electrolyte, which generally consists of a solution of a acetonitrile and of propylene carbonate solubilizing the redox mediator (iodide/iodine), is a chemically aggressive mixture which makes the "leaktight coating" of the two electrodes of the cell difficult.

This problem is even worsened by the release of gas which can occur inside the cell.

The operating temperature of a photovoltaic cell often exceeds 50° C. in sunshine and the volatility of the electrolyte solvents then generates an overpressure inside the assembly.

In addition, the rate of reduction of the triiodide ion at the counterelectrode is known to be the limiting step of the spectroelectrochemical cycle [4]. Because of the excessive corrosive nature of the iodine present in the liquid electrolyte, it is impossible to introduce metal wires that would be encapsulated in the transparent conductor, which is generally mixed tin or indium oxide or doped tin oxide, and that would make it possible to improve the charge transport in the exterior electric circuit. These secondary conducting wires, if they could be used, would prove to be very beneficial for draining the current from photovoltaic cells with a large surface area.

It was thus thought that the problems linked to the liquid electrolyte might be solved by using a solid conductor between the photocathode and the counterelectrode. Thus, it was thought that it might be possible to eliminate the problems of leaktightness and to increase the current density exchanged between the oxidized sensitizer and the counterelectrode.

Research studies have focussed on designing photovoltaic cells comprising pn-semiconductive materials, comprising both a solid n-semiconductive region and a solid p-semiconductive region consisting of organic materials.

Thus, patent application EP 1176646 describes photovoltaic cells comprising an n-semiconductive region consisting of a titanium oxide ceramic sensitized with inorganic semiconductive (semiconductor) nanoparticles and comprising a p-semiconductive region formed by a hole-conductive (hole-conducting) organic molecule belonging to the family of spiro and heterospiro compounds, in particular the molecule 2,2',7,7'-tetrakis(N,N-di-p-methoxyphenylamine)-9,9'-spirobifluorene (known by the abbreviation OMeTAD). This p-region is obtained by spin-coating the n-region using a solution comprising OMeTAD and chlorobenzene. However, the contact time during which the OMeTAD-containing solution is in contact with the titanium oxide layer is relatively short owing to the rapid evaporation of chlorobenzene and to the deposition method used. This results in particular in limited interpenetration of the n- and p-regions, this limited interpenetration also being due to the slow diffusion of the OMeTAD molecules towards the internal surface of the ceramic (namely the pore wall surface). This limited interpenetration of the n- and p-regions results in low solar efficiency.

Patent application EP 0 917 208 describes a photovoltaic cell comprising a photoactive film consisting of an organic polymer matrix based on poly(para-phenylene vinylene) (known by the abbreviation PPV) in which semiconductive (semiconductor)-type nanoparticles (particularly $TiO_2$) are dispersed. In this configuration, the PPV provides the hole conduction function (i.e. the function of a p-semiconductive-semiconductor-region) and the function of a chromophore substance, by absorbing the photons from the light, whereas the dispersed nanoparticles provide the electron conduction role (n-semiconductive-semiconductor-region). However, this type of configuration has the following drawbacks:
the dispersion of nanoparticles in the organic matrix limits the percolation of the nanoparticles and thus limits the conduction of electrons to the electron-collecting layer of the photovoltaic cell; and
the dispersion of nanoparticles in the organic matrix results in a high rate of electron-hole recombination at the PPV/nanoparticles interface.

Patent application WO 93/20569 describes a dye-based photovoltaic cell comprising a region formed by a porous titanium oxide film sensitized with a chromophore substance and a region consisting of a hole-conducting polymer. The method of producing this type of photovoltaic cell consists in depositing, at high temperature (of the order of 300° C.), the conducting polymer in the molten state onto the porous titanium oxide film. However, the material obtained has the following drawbacks:
it is characterized by interpenetration between the porous film and the polymer that is limited by the diffusion of the polymer in the molten state into the porosity of the titanium oxide film;
it comprises a loose junction between the n-semiconductive (semiconductor) material and the p-semiconductive (semiconductor) material due to the fact that the bonding between these two regions takes place by weak interactions of the Van der Waals type; and
the operation carried out at high temperature (of the order of 200 to 300° C.) can damage the chromophore substance and prevent the use of a wide range of chromophore substances having low decomposition temperatures.

Several other publications relate to the same approach consisting in using a solid conductor.

To this effect, various solid conductors have been tested; they are inorganic materials such as CuI [5] or CuSSN [6][7], organic polymers such as polypyrrole [8][9][10] or polythiophene [11] to [21], or else small organic molecules such as aromatic tertiary amines [22] to [25]. These organic or inorganic films play the role of charge transporter between the counterelectrode and the sensitizer. The $TiO_2$ photoanode is impregnated beforehand with the sensitizer and is then coated with a film composed of an electrically conducting material (molecule or polymer). The most advantageous result is probably that published by Grätzel [22]. However, none of the systems described is satisfactory since the efficiency of the cell drops very substantially compared with a conventional cell comprising a liquid electrolyte; at best, this drop is by a factor of 20.

It may be assumed that the limited performances of these photovoltaic cells, and in particular their drop in efficiency, are due in particular to one or more of the following drawbacks:
limited interpenetration of the n-semiconductive (semiconductor) region and of the p-semiconductive (semiconductor) region;
high rate of electron-hole recombination at the junction between these regions due to the low interpenetration of the various n-region/chromophore/p-region components.

In other words, it may be thought that the drop in efficiency of the solid cell is due to inefficient electron transfer between the sensitizer dye and the solid electrical conductor.

This could be explained by poor adsorption of the p-semiconductor onto the sensitizer and also by poor wetting of the nanocrystalline network of the semiconductor by the electrical conductor, linked to the diffusion of this material into the pores of the semiconductor not being very deep [11][26].

In view of the above, there exists therefore, in general, a need for a photovoltaic cell which has improved performance levels and in particular an increased efficiency compared with the solid electrolyte photovoltaic cells of the prior art.

There also exists a need for a cell which can be readily provided with conducting wires immersed in the transparent conductor in order to drain the charges in the external electric circuit.

There exists in particular a need for a pn-type semiconductive material which exhibits a strong interaction and a strong interpenetration between the p-semiconductive (semiconductor) region and the n-semiconductive (semiconductor) region, while at the same time allowing, however, the short-circuit phenomena between the two regions to be limited.

In other words, there exists a need to increase the electron transfer efficiency between the sensitizer dye and the solid electrical conductor and to improve the wetting of the nanocrystalline network of the semiconductor such as $TiO_2$ by the electrical conductor.

The objective of the present invention is to provide a sensitizer, a pn-type semiconductive material and a photovoltaic cell which meet, inter alia, the needs listed above.

The objective of the present invention is also to provide a sensitizer, a pn-type semiconductive material and a photovoltaic cell which do not have the drawbacks, limitations, faults and disadvantages of the sensitizers, pn-type semiconductive materials and photovoltaic cells of the prior art and which solve the problems which are stated in the prior art.

DETAILED DESCRIPTION OF THE INVENTION

This objective, and others, are achieved in accordance with the invention by means of a complex of formula (I)

 (I)

in which:
F represents one or more groups capable of grafting chemically to a substrate of semiconductive porous oxide ceramic;
S represents a sensitizing group (sensitizer) for (sensitizing) a semiconductive porous oxide ceramic;
C is an electrically conductive (conducting) polymer;
E is a deconjugating spacer group which makes it possible to electrically isolate the sensitizer (S) from the electron-conductive (electron-conducting) polymer (C).

Said complexes of formula (I) according to the invention are novel compounds which are fundamentally different, in particular from the sensitizer compounds of the prior art. In fact, these complexes have, in a completely novel manner, a structure in which a sensitizing group S (sensitizer) and a conductor group are connected by means of a non-conjugated covalent bond E.

Such compounds having such a specific structure are neither described nor suggested in the prior art. Surprisingly, the inventors have associated, in the same molecule, i.e. the complex of formula (I), a sensitizer S and a conductive polymer C and, furthermore, even more surprisingly, they have separated S and C by means of a deconjugating spacer group.

The novel complexes according to the invention play, surprisingly, both the role of sensitizer and the role of electrically conductive polymer. Associating these two functions in the same molecule is unexpected.

The complexes of the invention may be defined as sensitizers functionalized with a molecule for transporting electric charges, i.e. the conductive polymer C.

If the length of this molecule is sufficient, as is the case of the polymers C of the complexes of the invention, it "will go beyond" (emerge from) the pores of the nanoporous structure of the semiconductor. Thus, all the sensitizers will be in electrical contact with the solid conductive material deposited at the surface of the photoanode.

Another important novel structural characteristic of the complexes according to the invention is the insertion of a deconjugating unit between the sensitizer and the conductive polymer, which makes it possible to conserve the intrinsic electronic properties of the sensitizer after it has been functionalized with the conductive polymer. Thus, the injection yield of the electron into the semiconductor from the excited state of the sensitizer is conserved after the grafting of the chain of conductive polymer C.

The grafting of the novel complexes according to the invention—comprising a sensitizer group linked via a non-conjugated covalent bond to a chain of a conductive polymer—such as a polythiophene or a derivative thereof on a conductive electrode coated with an n-semiconductor having a wide band gap, such as $TiO_2$, $ZnO$ or $SnO_2$, optionally followed by the depositing of a film of a p-charge conductor such as a conductive polymer chosen in particular from polythiophenes, polypyrroles and respective derivatives thereof, or of small organic molecules, and finally by the depositing of a metal electrode, for example made of gold, silver or aluminium, results in increased efficiency of the photocell.

The sensitizer-conductive polymer complex according to the invention constitutes a novel material which makes it possible to improve the transfers.

Document [31] discloses complexes of F—S—C type which can be adsorbed onto macroporous anatase electrodes. The complexes described in this document do not, like the complexes of formula (I) according to the invention, comprise a deconjugating spacer group E.

The introduction of a spacer E results in novel compounds that are fundamentally different from those which are encountered in [31]. The presence of a spacer E plays a fundamental role in charge injection processes, responsible for photovoltaic phenomena.

Document [32] describes a pn-semiconductor (semiconductive) material that can be obtained by means of the following successive steps:
functionalization of a (semiconductive) semiconductor porous oxide ceramic, by chemical grafting of one or more compounds comprising a group that can be polymerized with one or more precursors of an electrically conductive polymer, and at least one group capable of grafting chemically to said substrate;
impregnation of said functionalized substrate with a solution comprising said precursor(s);
polymerization of said precursors.

It is mentioned that this material may optionally comprise one or more chromophore substances which sensitize said ceramic.

It is specified that this substance may be either absorbed or chemically grafted to the surface and to the inside of the oxide ceramic substrate.

The chromophore is not integrated into the complex (like the group S of our complex), but is directly attached to the surface and to the inside of the ceramic substrate.

Spacer groups corresponding to the groups E of the materials according to the invention are optionally present in the materials of document [32], i.e. are not necessarily present in the materials of document [32].

It is also indicated that the spacer group ("E") can separate the polymer from the groups capable of chemically bonding: this group "E" which is optional does not therefore separate, as in our complex, the polymer from the sensitizer, chromophore group.

Finally, a complex of formula (I) according to the invention cannot be prepared and cannot exist as such in document [32] since, in this document, the semiconductive (semiconductor) material is prepared by successive steps of synthesis from the ceramic.

The basic idea of our invention consists in designing compounds in which the species participating in the charge transport are no longer either superimposed or even built into intimate contact, but are physically linked by covalent bonds.

However, we have established that grafting the polymer onto the sensitizer without a spacer, as described in [31], radically modifies the electronic properties of the sensitizer. In fact, in this case, the electron levels of the excited states of the ligand, for example terpyridine ligand, bearing the conductive polymer are lowered in such a way that the electrons are transferred to the conductive polymer and no longer to the semiconductor, for example n-semiconductor, which is highly detrimental to the photovoltaic efficiency (see attached examples).

In order to remedy this drawback, we show, according to the invention, that it is necessary to introduce a deconjugating link between the sensitizer and the conductive polymer. This has the effect of conserving the electronic properties of the sensitizer while at the same time allowing charge transfer to the conducting polymer. For this, it is advisable to preferably use weakly deconjugating links such as —$CH_2$—$CH_2$— functions or substituted aromatic rings (twisting of the ring outside the plane of overlap of the pi orbitals due to steric hindrances). Surprisingly, the introduction of the deconjugating link is not detrimental to the charge transfer to the conductive polymer.

The introduction of the deconjugating spacer therefore has the effect of restoring the properties of the sensitizer, while at the same time allowing charge transfer to the grafted conductive polymer.

Before describing the invention in greater detail, we will specify the following definitions:

The expression "semiconductive (semiconductor) substrate to which the complex of formula (I) is grafted" is intended to mean generally the porous oxide ceramic which is part of a pn-semiconductive inorganic/organic hybrid material comprising a porous oxide ceramic to which the complex of formula (I) is chemically grafted.

Said pn-type semiconductive inorganic/organic hybrid material is described below; it comprises an n-type semiconductive (semiconductor) region and a p-type semiconductive (semiconductor) region. In the context of the invention, the n-type semiconductive region, preferably having a wide band gap, may consist of said substrate of porous oxide ceramic, in which case the p-type semiconductive region will consist of the electrically conductive polymer(s).

Alternatively, the n-type conducting region may consist of the electrically conductive polymer(s), in which case the p-type semiconductive region of said hybrid material consists of the porous oxide ceramic substrate.

It is also specified that this substrate may be in the form of a block (or a piece) or else in the form of a coating (for example a film having a thickness of 10 nm to 100 µm).

The expression "electrically conductive (conducting) polymer" is intended to mean a polymer having electrical conduction properties without being doped (in which case the polymer will be an intrinsically electrically conductive polymer) or when it is doped (in which case the polymer will be an extrinsically electrically conductive polymer), the electrical conduction being provided either with electrons (with regard to n-type conductive polymers), or by holes which correspond to "spaces" left vacant by electrons (with regard to p-type conductive polymers). Specific examples of these various types of polymers will be given later.

Both in the foregoing text and in the text that follows, the expression "chemical grafting" is intended to mean immobilization of the abovementioned complex compound(s) of formula (I) on the abovementioned substrate by means of a covalent, or even ionic-covalent, chemical bond. It is specified that this immobilization takes place both on the external surface of the substrate and also the internal surface of said substrate, i.e. on the surface of the pore walls of the substrate. It is clearly understood that the chemical grafting does not exclude the existence of simple physical interactions such as "Van der Waals" interactions or interactions of hydrogen bond type between the abovementioned compounds and the abovementioned substrate.

The expression "group capable of grafting chemically to said substrate" is intended to mean groups which react with the reactive groups present on the oxide ceramic, such as —OH groups, these —OH groups resulting from a phenomenon of spontaneous hydration of the ceramic, either under the effect of ambient atmospheric moisture, or under the effect of moisture caused in order to create these groups.

The group(s) capable of grafting chemically to the ceramic may be chosen from the groups of formulae below:

$COOR^1$ with $R^1$ representing a hydrogen atom, an alkyl group comprising from 1 to 30 carbon atoms or a phenyl group;

COCl;

$COCH_2CO$—$R^1$ with $R^1$ representing a hydrogen atom, an alkyl group comprising from 1 to 30 carbon atoms or a phenyl group;

$PO(OH)_2$, —$PO(OR^2)(OH)$ or —$PO(OR^2)(OR^3)$ with $R^2$ and $R^3$, which may be identical or different, representing an alkyl group comprising from 1 to 30 carbon atoms or a phenyl group;

CO(NHOH);

$M(OR^4)_{m-x}Z_x$ with x being an integer ranging from 1 to (m−1), M being a metal or a metalloid, m being an oxidation number of M, $R^4$ representing a hydrogen atom, an alkyl group comprising from 1 to 30 carbon atoms, a phenyl group, a monovalent metal cation, or a group of formula $N^+R^1_4$, with $R^1$ representing a hydrogen atom, an alkyl group comprising from 1 to 30 carbon atoms, or a phenyl group, and Z represents a hydrogen atom, an alkyl group comprising from 1 to 30 carbon atoms, a phenyl group or a halogen atom;

$SO_3M'$ with M' representing a hydrogen atom, a monovalent metal cation or a group of formula $N^+R^1_4$ with $R^1$ representing a hydrogen atom, an alkyl group comprising from 1 to 30 carbon atoms or a phenyl group;

$B(OM')_2$ with M' representing a hydrogen atom, a monovalent metal cation or a group of formula $N^+R^1_4$ with $R^1$ representing a hydrogen atom, an alkyl group comprising from 1 to 30 carbon atoms or a phenyl group;

OH;

and combinations thereof.

In the group of formula $-M(OR^4)_{n-x}Z_x$ as defined above, M may represent a metal element, such as a transition element of given oxidation number n or a metalloid element, such as Al, Ga, In or Si, of given oxidation number n, the conceivable oxidation numbers for each metal or metalloid element being known to the man skilled in the art. As example of a group in accordance with this definition, mention may be made of the group of formula: —$Si(OR^4)_{3-x}Z_x$ with x being an integer from 1 to 3.

The chemical grafting with the porous oxide ceramic substrate advantageously takes place by means of the groups listed above.

The complex according to the invention comprises a sensitizer group S for sensitizing the semiconductive (semiconductor) substrate, for example the n-type semiconductive (semiconductor) substrate having a wide band gap, which is the oxide ceramic.

This group may also be referred to as chromophore group for sensitizing said ceramic.

It is specified that, according to the invention, the expression "chromophore substance" is intended to mean a substance able to absorb light in the IR, UV and visible range and to release electrons in return for this absorption. In the context of the invention, the electrons will be captured either by the oxide ceramic (if this is an n-semiconductor) or by the electrically conductive polymer(s) (if these are n-type polymers), whereas the charge holes left by the released electrons are captured either by the oxide ceramic (if this is a p-type semiconductor) or by the electrically conductive polymer(s) (if these are p-type polymers).

It is understood that a given chromophore substance has a well-defined spectral sensitivity and that the choice of this substance must be tailored to the light source, so as to have the highest possible light absorption efficiency.

Said sensitizing group S (sensitizer) may be chosen, for example, from polypyridine complexes with a transition metal and organic cations such as phthalocyanins, coumarins and cyanins.

Advantageously, said sensitizing group is a group of formula (II) or of formula (IIA):

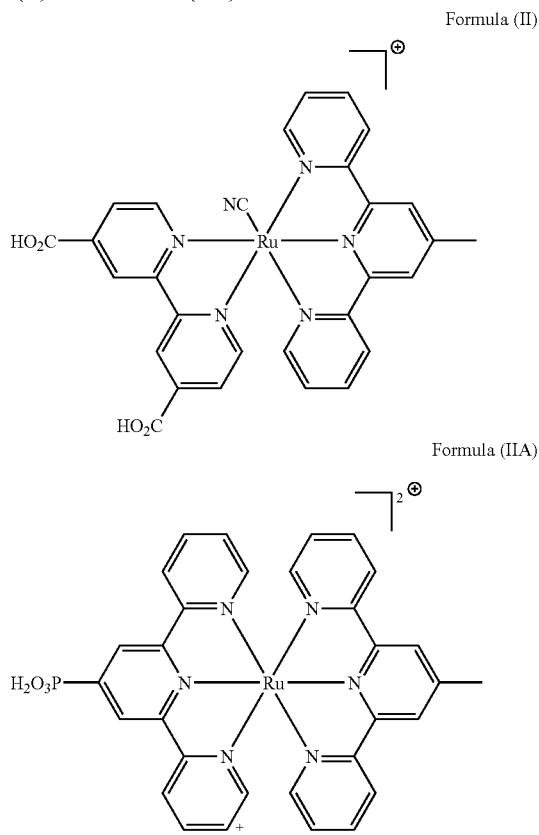

Formula (II)

Formula (IIA)

The electrically conductive polymer C is generally chosen from poly(acetylene)s, poly(p-phenylene)s, poly(p-phenylene vinylene)s, poly(p-phenylene sulphide)s, poly(pyrrole)s, poly(thiophene)s, poly(alkylthiophene)s, poly(dialkylthiophene)s, poly(alkoxythiophene)s, poly(furan)s, poly(azulene)s, poly(azine)s, poly(aniline)s, poly(cyanophenylene vinylene)s, poly(para-pyridyl vinylene)s, and poly(dioxythiophene)s ("PEDOT"), the repeating unit of which corresponds to the formula below:

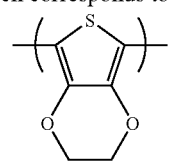

and blends and/or combinations and/or copolymers thereof (i.e. the copolymers formed from the monomers constituting the above polymers, with one another, or with other monomers).

Among this list of polymers, the n-type polymers are poly(cyanophenylene vinylene)s and poly(p-pyridyl vinylene)s.

Among this list of polymers, the p-type polymers are poly(p-phenylene)s, poly(p-phenylene vinylene)s, poly(p-phenylene sulphide)s, poly(pyrrole)s, poly(thiophene)s, poly(alkylthiophene)s such as poly(3-octylthiophene), poly(dialkylthiophene)s such as poly(3,4-dioctylthiophene)s, poly(alkoxythiophene)s, poly(furan)s, poly(azulene)s, poly(azine)s, poly(aniline)s and poly(dioxythiophene)s.

Advantageously, said p-type electrically conductive polymer C is a regioregular polymer such as a "regioregular" poly(alkylthiophene), for example poly(3-octylthiophene).

The electrically conductive polymer C may in particular be chosen from the following polymers:

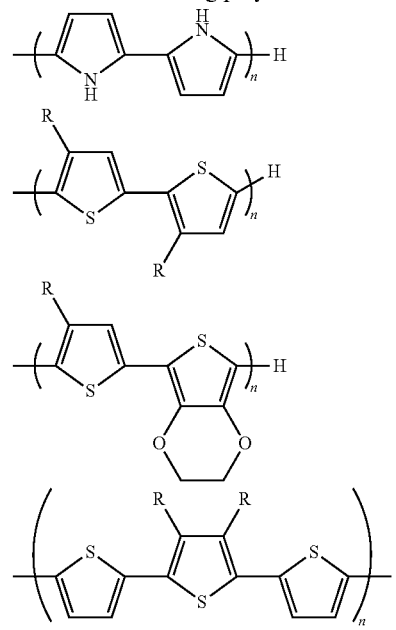

where n represents an integer from 1 to 1 000, preferably from 5 to 100, and R represents a group chosen from alkyl groups having from 1 to 24 carbon atoms, preferably from 4 to 12 carbon atoms, and alkoxy groups having from 1 to 24 carbon atoms, preferably from 4 to 12 carbon atoms.

The deconjugating spacer group E is a fundamental structural element of the dyes, complexes according to the invention.

The term "spacer" is generally intended to mean a unit consisting of at least one atom, separating two functional entities.

The term "deconjugating" is generally intended to mean that the group produces a breaking (rupture) of the conjugation by breaking (rupture) of the overlap of the π orbitals.

The groups which may be suitable for such deconjugating spacer groups may be readily determined by the man skilled in the art. Thus, said deconjugating spacer group E may be chosen from the groups:

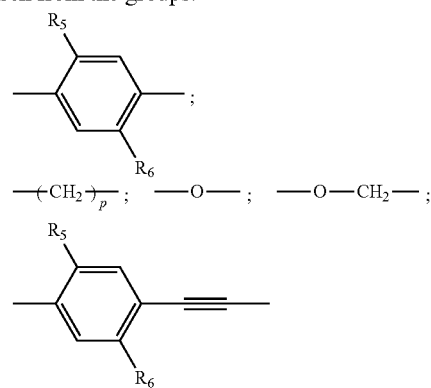

where $R_5$ and $R_6$, which may be identical or different, are generally chosen, inter alia, from alkyl groups having from 1 to 24 carbon atoms, preferably from 1 to 12 carbon atoms, and alkoxy groups having from 1 to 24 carbon atoms, preferably from 1 to 12 carbon atoms; p is an integer from 1 to 20, preferably from 1 to 4.

The dyes, complexes, that are preferred according to the invention correspond to formula (III) or to formula (IIIA) below:

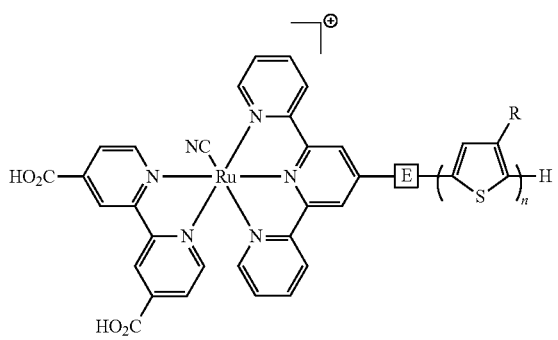

Formula (IIIA)

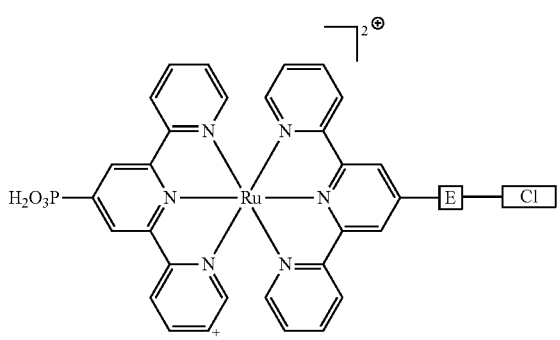

in which n represents an integer from 1 to 1 000, preferably from 5 to 100; R represents an alkyl group having from 1 to 24 carbon atoms, preferably from 4 to 12 carbon atoms, or an alkoxy group having from 1 to 24 carbon atoms, preferably from 4 to 12 carbon atoms, and E is chosen from the groups.

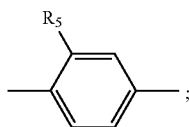

$R_5$ and $R_6$, which may be identical or different, are chosen from alkyl groups having from 1 to 24 carbon atoms, preferably from 1 to 12 carbon atoms, and alkoxy groups having from 1 to 24 carbon atoms, preferably from 1 to 12 carbon atoms; and C1 represents:

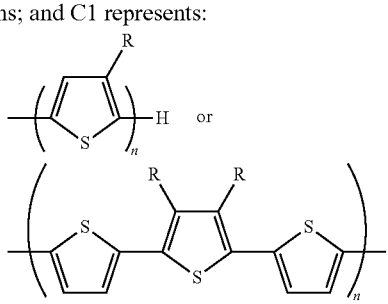

The invention also relates to a process for preparing the preferred compounds (III) described above, where E represents —$(CH_2)_2$— or

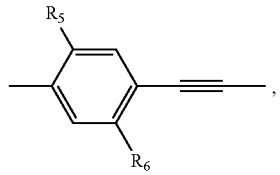

in which the following successive steps are carried out:
a)—a compound of formula 1 below or of formula 12 below:

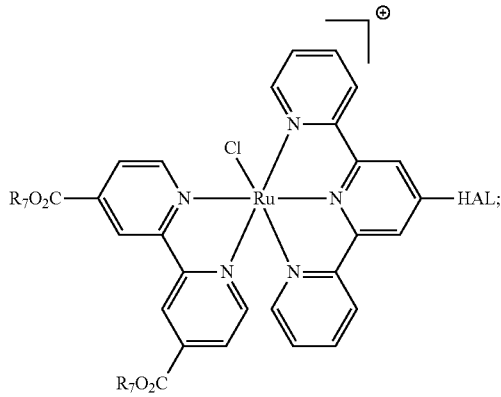

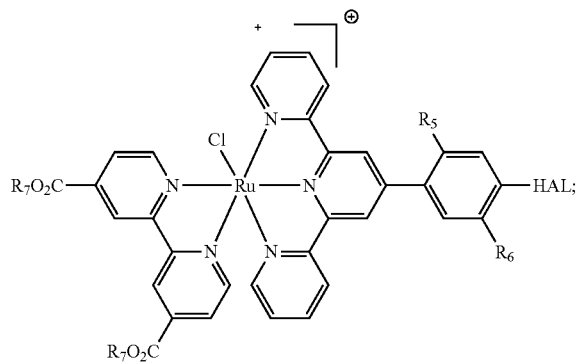

is reacted with a compound of formula 2 below:

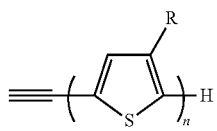

in which n represents an integer from 1 to 1 000, preferably from 5 to 100, and R, $R_5$, $R_6$ and $R_7$, which may be identical or different, represent an alkyl group having from 1 to 24 carbon atoms, preferably from 4 to 12 carbon atoms for R, and preferably from 1 to 12 carbon atoms for $R_5$, $R_6$ and $R_7$, or an alkoxy group having from 1 to 24 carbon atoms, preferably from 4 to 12 carbon atoms for R, and preferably from 1 to 12 carbon atoms for $R_5$, $R_6$ and $R_7$, more preferably $R_7$ is an ethyl group, and HAL represents a halogen atom, preferably a Br atom; according to a SONOGASHIRA reaction, in a mixture of DMF/THF, in the presence of a catalytic system comprising copper iodide, [1,1'-bis(diphenylphosphino)ferrocene] dichloropalladium (II) and triethylamine, so as to obtain respectively a compound of formula 3 below, or a compound of formula 13 below:

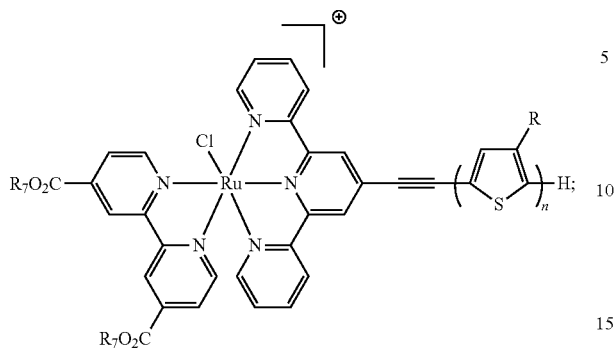

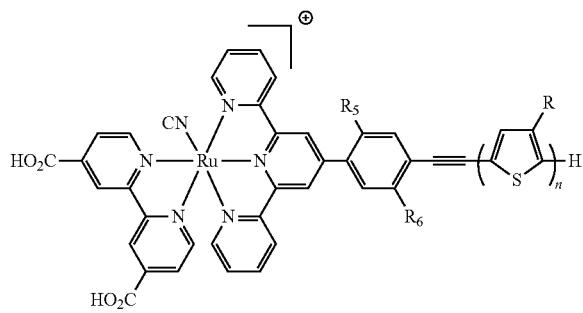

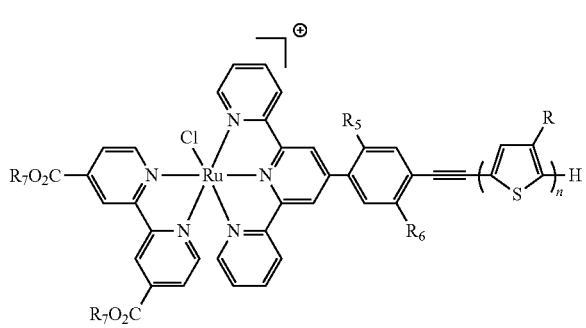

b)—the compound of formula 3 is reacted with hydrogen in THF in the presence of palladium-on-charcoal, so as to obtain a compound of formula 4 below:

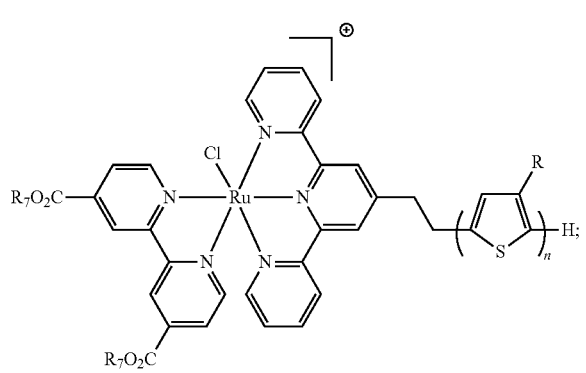

c)—the compound of formula 4 or the compound of formula 13 is reacted, in a mixture of THF/H$_2$O with KCN/LiOH, so as to obtain respectively a compound of formula 5 below or a compound of formula 14 below:

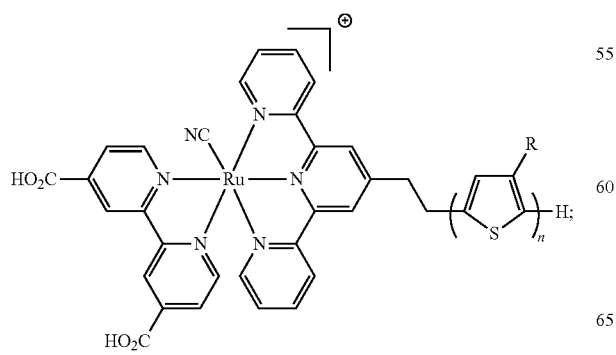

It should be noted that this process can also be carried out for preparing the compounds of formula (IIIA), in return for some adjustments and adaptations within the scope of the man skilled in the art.

The compound of formula 12 above can be prepared by reacting a compound 10

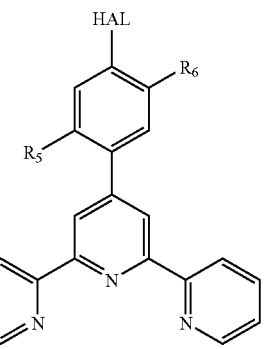

where HAL represents a halogen atom, preferably a Br atom, with a compound 11

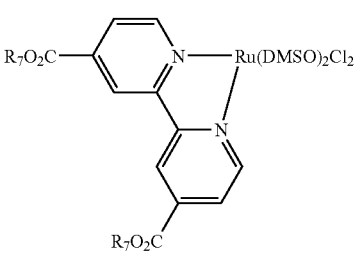

The invention also relates to a compound

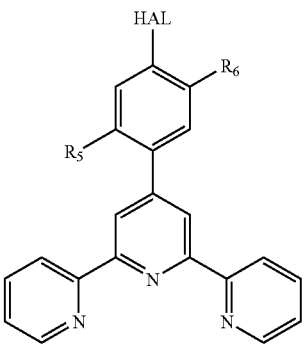

where HAL represents a halogen atom, preferably a Br atom, which is a new intermediate compound.
The schemes below illustrate the routes for synthesizing the compounds of formula (III):
Scheme 1: synthesis of molecule 5
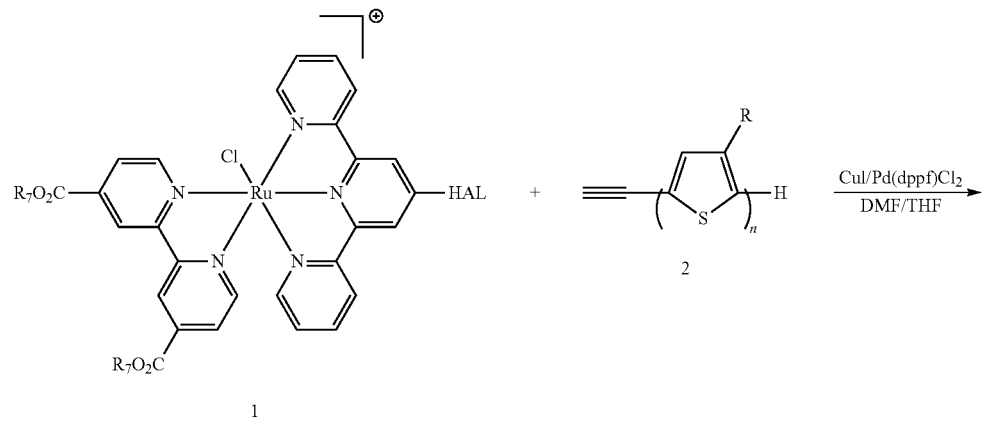
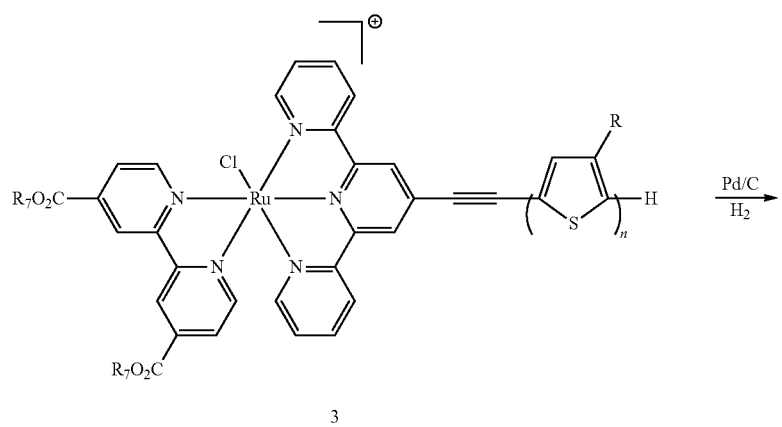
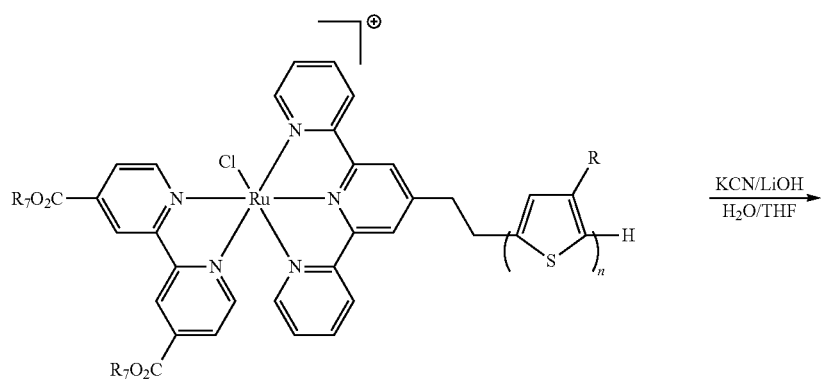

-continued
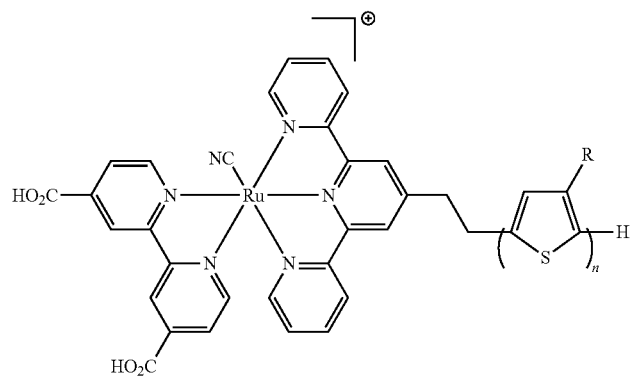
5
(R and R7 represent an alkyl or alkoxy chain containing from
1 to 24 carbon atoms, and preferably from 4 to 12 carbon atoms for R,
or preferably from 1 to 12 carbon atoms for $R_7$; $R_7$ is more preferably Et).
Scheme 2: preparation of compound 14.
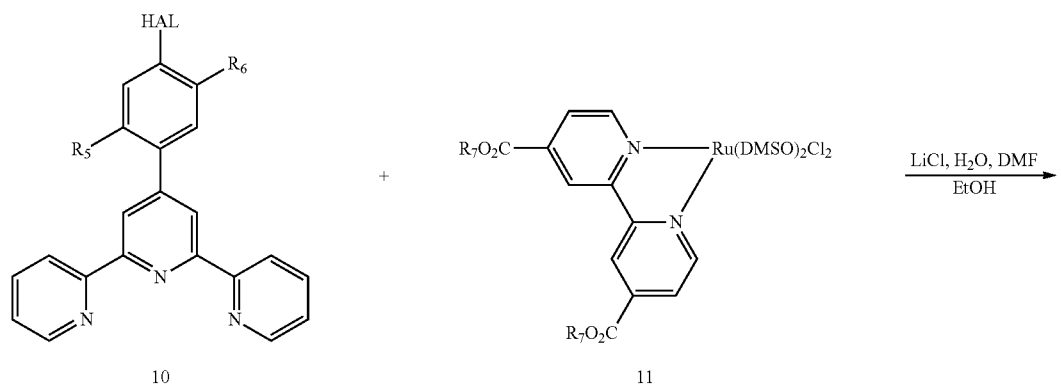
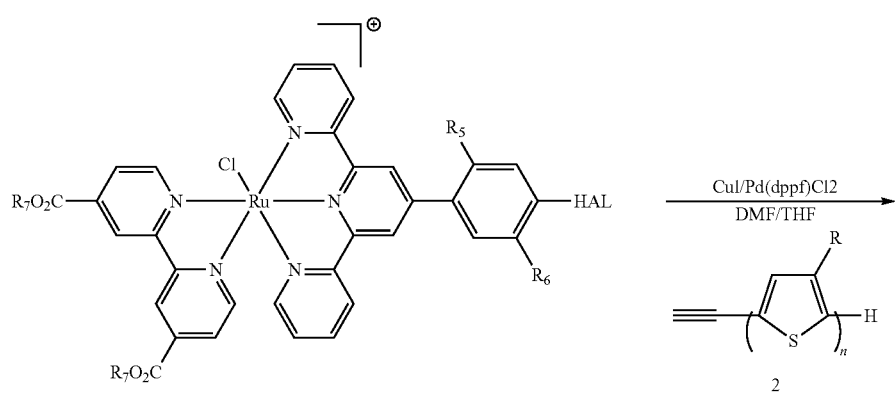

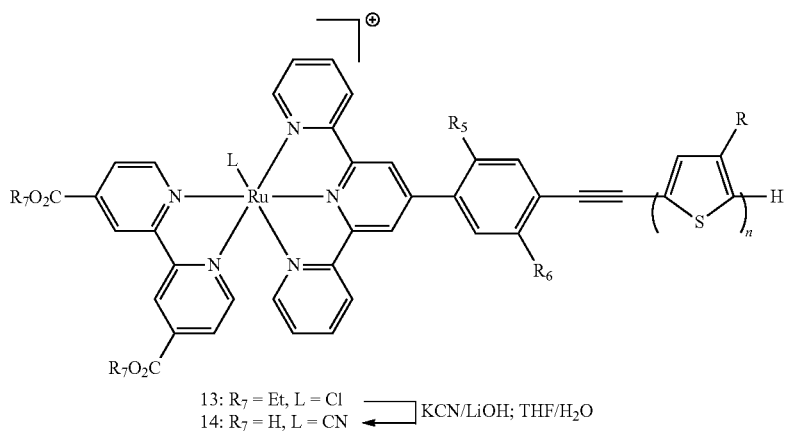

13: $R_7$ = Et, L = Cl
14: $R_7$ = H, L = CN   ← KCN/LiOH; THF/H$_2$O

R, $R_5$, $R_6$, $R_7$ represent an alkyl or alkoxy chain containing from 1 to 24 carbon atoms, preferably from 4 to 12 carbon atoms for R, and preferably from 1 to 12 carbon atoms for $R_5$, $R_6$ and $R_7$; $R_7$ is more preferably Et, and in compound 14, $R_7$, by way of exception, represents H.

The complex 1 is prepared according to a protocol from the literature described by Odobel [29] and the polymer 2 is, for its part, obtained according to a method published by McCullough [30]. The grafting of 1 onto 2 is carried out by a Sonogashira reaction with the Pd(dppf)Cl$_2$ catalyst (dppf=diphenylephosphoferrocene).

The synthesis of the complex 14 is carried out according to a series of reactions similar to that for preparing 5 from the complex 12 and from the polymer 2.

12 is prepared from the complex 11 described by Odobel [29] (scheme 2) and from the ligand 10.

The new ligand 10 is prepared according to the reaction sequence illustrated in scheme 3. The molecule 9 is synthesized from the commercially available precursors 6 and 7 by condensation of the aldehyde 8 and of the acetyl pyridine 7. Cyclization of the pyridone 9 with ammonium acetate produces the terpyridine 10.

Scheme 3: synthesis of the terpyridine 10;

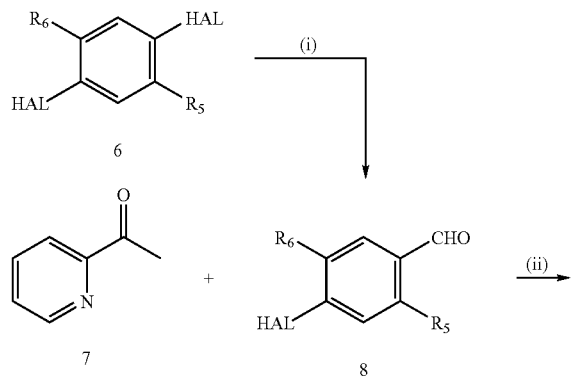

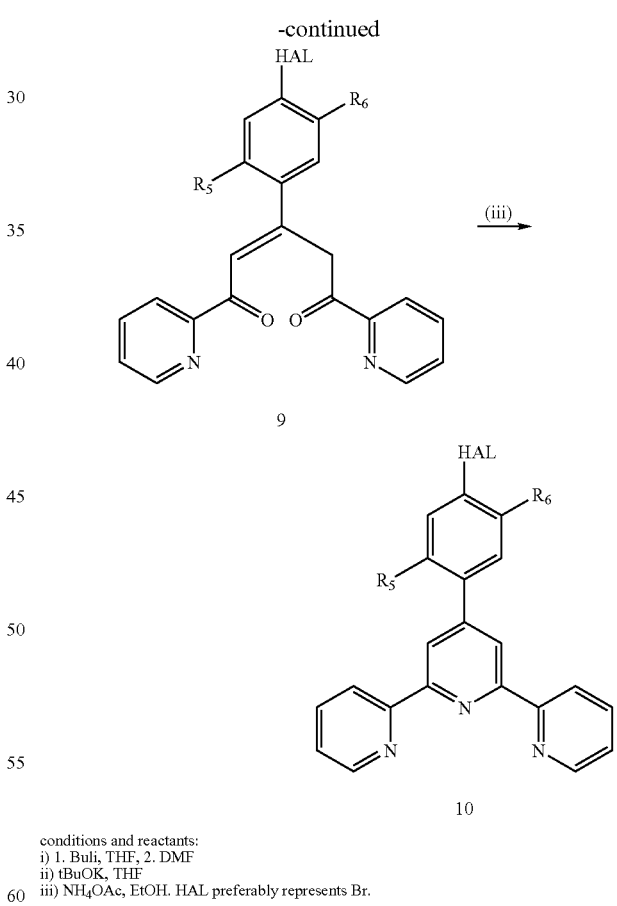

conditions and reactants:
i) 1. Buli, THF, 2. DMF
ii) tBuOK, THF
iii) NH$_4$OAc, EtOH. HAL preferably represents Br.

The complex 12' can also be readily obtained by hydrolysis of the complex 12. This complex can be used without polymer grafting. However, the grafting of a conductive polymer in accordance with the invention makes it possible to substantially increase the photovoltaic efficiencies.

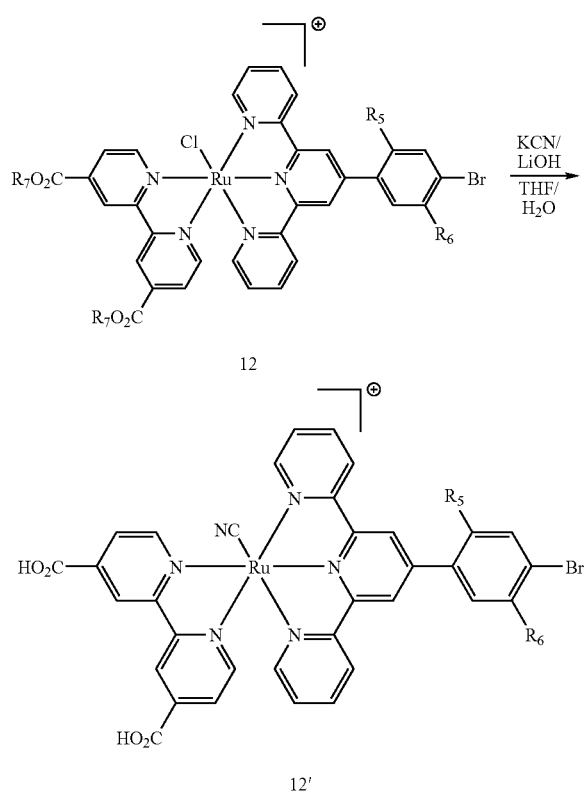

$R_5$, $R_6$ and $R_7$ are as defined above. Preferably, $R_7$ is ethyl.

The invention also relates to a pn-type semiconductive (semiconductor) inorganic/organic hybrid material comprising a semiconductive (semiconductor) porous oxide ceramic to which a dye, complex of formula (I), as defined above, is chemically grafted.

This material is new and has advantageous properties linked to the complex of formula (I) which have already been described above.

As was mentioned above, the substrate is a semiconductive (semiconductor) porous oxide ceramic. It is understood that, depending on whether the electrically conducting polymer(s) is (are) n-type polymers or p-type polymers, the oxide ceramic will be chosen so as to be of the p-type or n-type, this choice being within the understanding of the man skilled in the art. The oxide ceramics may be ceramics based on transition metals chosen from Ti, V, Cr, Mn, Fe, Co, Ni, Cu, Zn, Y, Zr, Nb, Mo, Ru, Rh, Pd, Ag, Cd, Hf, Ta, W, Re, Os, Ir, Pt, or based on lanthanides, such as La, Ce, Pr, Nd, Sm, Eu, Gd, Tb, Dy, Er, and Yb, or based on elements of group IIIA of the Periodic Table of Elements, chosen from Al, Ga, In and Tl, or based on elements of group IVA of the Periodic Table of Elements, chosen from Si, Ge, Sn and Pb, or based on elements of group VIA of the Periodic Table of Elements, chosen from Se and Te. The oxide ceramics may also be any combination of transition metals, lanthanides, elements of group IIIA, elements of group IVA and elements of group VIA.

For the purpose of the present invention, the expression "porous oxide ceramic" is intended to mean a metallic ceramic having oxygen atoms and having an overall open porosity. Suitable ceramics may be amorphous, nanocrystalline and/or mesoporous oxide ceramics.

The term "amorphous oxide ceramic" is intended to mean a ceramic having no crystallites, or crystallites of sub-nanoscale size.

The term "nanocrystalline oxide ceramic" is intended to mean a ceramic having crystallites of the order of a few nanometers, for example from 2 to 200 nm.

Finally, the term "mesoporous oxide ceramic" is intended to mean a ceramic characterized by a high porosity, with pore sizes ranging from 2 to 80 nm and walls of from 5 to 30 nanometers in thickness. In general, the pores are randomly distributed with a very broad pore size distribution, within the range mentioned above. The mesoporous ceramics used according to the invention are advantageously "mesostructured" ceramics, which are in the form of organized porous networks that have an ordered spatial arrangement of mesopores. This spatial periodicity of the pores is characterized by the appearance of at least one low-angle peak in an X-ray scattering pattern; this peak is associated with a repeating distance of generally between 2 and 50 nm. The mesostructured materials are characterized by a maximized surface area for a given volume and by the certainty of the continuity of the solid network along at least one direction in space through the walls constituting said material.

An example of a porous oxide ceramic that can be used according to the invention is titanium dioxide $TiO_2$. Other examples are $ZnO$ or $SnO_2$.

Among the ceramics contemplated in the above paragraph, the man skilled in the art may choose n-type ceramics (in which case the conducting polymer C grafted by means of the complex according to the invention will be a p-type polymer) and/or p-type ceramics (in which case the conducting polymer grafted by means of the complex according to the invention will be an n-type polymer).

In the hybrid material according to the invention, the surface and also the interior of the porous ceramic substrate is grafted, with one or more complexes defined above which comprise an electrically conductive polymer as defined above.

The invention also relates to a process for preparing the semiconductive (semiconductor) inorganic/organic hybrid material as defined above, in which a semiconductive (semiconductor) porous oxide ceramic is impregnated with an organic solution comprising one or more complexes of formula (I) as defined above.

As specified above, in the hybrid material according to the invention, a porous oxide ceramic surface is grafted with compounds of formula (I) as defined above, said compounds being grafted chemically to said surface of the ceramic.

To obtain such a grafting, various techniques may be envisaged, in particular liquid processing techniques, i.e. techniques in which the abovementioned semiconductive (semiconductor) porous oxide ceramic substrate is impregnated with an organic solution comprising the compound(s) of formula (I) as defined above.

Thus, the chemical grafting to the surface and to the interior of the porous oxide ceramic may be carried out by one of the following techniques:
dip coating;
spin coating;
laminar-flow coating;
spray coating;
soak coating;
roll-to-roll coating;
brush coating;
screen printing.

These various techniques should be employed for a suitable time, so as to allow optimum contact between the porous oxide ceramic substrate and the solution comprising the compound(s) (I) able to be grafted, so that the substrate is impregnated both on its surface and on its interior and so that the compounds can react and be chemically bonded to the surface and to the interior of said substrate. For example, this time may be from 1 to 48 hours, for example 16 hours.

The solvent of said solution may be readily chosen by those skilled in the art.

This solvent may thus be chosen from THF, aliphatic alcohols containing from 1 to 4 carbon atoms, such as methanol and ethanol, halogenated solvents, and mixtures thereof.

The concentration of the dye complex (I), in said solution, can be readily determined by those skilled in the art; it is generally from $10^{-3}$ to 1 M.

The temperature at which the impregnation is carried out can similarly be readily determined by those skilled in the art; it is generally from 20 to 80° C., and this impregnation is preferably carried out at ambient temperature.

After this grafting or functionalization step, the process for preparing the inorganic/organic hybrid material according to the invention may comprise a treatment step intended to remove the grafting reaction residues and also the species that have not reacted.

This treatment may consist in rinsing the hybrid material with an aqueous or organic solvent which is preferably the same solvent as that used for the grafting.

Finally, drying of the inorganic/organic hybrid material is generally carried out.

The semiconductive (semiconductor) inorganic/organic hybrid materials of the invention may be used in various devices requiring the presence of a semiconductive (semiconductor) material, such as electrochemical devices, photoelectrochemical devices and catalytic devices, and in particular in photovoltaic cells or light-emitting diodes.

Thus, a subject of the present invention is also a photovoltaic cell comprising:

a current-collecting first electrode (called a "working electrode");

a second electrode (called a "counterelectrode"); and a semiconductive region consisting of the semiconductive hybrid material as defined above, said region being placed between said first electrode and said second electrode.

The first electrode, or working electrode, comprises a conductive (conducting) portion, for example in the form of a layer of fluorine-doped tin oxide, or of ITO, this portion possibly being deposited on a support.

It is specified that, the term "support" is intended to mean, for the purpose of the invention, any organic or inorganic substrate, characterized by a transparency of at least 50% in the solar spectrum. This support may, for example, be made of transparent glass.

It should be noted that the abovementioned conductive portion will be in contact with the abovementioned semiconductive (semiconductor) region, either directly or via, for example, a dense titanium dioxide layer, the latter making it possible to prevent direct contact between the working electrode and the semiconductive (semiconductor) region and consequently to prevent a short circuit in the photovoltaic cell.

It is also specified that a layer based on an electrically conductive polymer or on another p-type conductive molecule may be interposed between said semiconductive region made of semiconductive hybrid material according to the invention and the second electrode (called "counterelectrode"), so as to prevent a short circuit in the photovoltaic cell.

In fact, in general, the "FSEC" complex of formula (I) is self-sufficient, i.e. the length of the chain of the polymer C is sufficient to emerge from the pores of the porous oxide ceramic material and to ensure contact with the second electrode. In this case, said layer of electrically conductive polymer is not necessary.

It is, however, probable that, in certain cases, the chain C will not be long enough, in which case the active hybrid material is coated with a solid p-type (or n-type) conductive material generally consisting of an electrically conductive polymer such as a regioregular poly(alkylthiophene), for instance poly(3-octylthiophene), or of another p-type conductive molecule such as an aromatic amine.

Preferably, an electrically conductive polymer identical to the electrically conductive polymer C of the complex (I) which is part of the semiconductive (semiconductor) hybrid material, such as a poly(3-octylthiophene), is chosen for this additional layer.

Said optional additional layer of electrically semiconductive polymer can be prepared by any suitable technique, for example by a wet processing technique as already described above, for example a technique which uses a solution of the polymer in a solvent, such as spin coating.

In general, the second electrode (or "counterelectrode") is in the form of a metal layer, for example a metal layer based on gold and/or on nickel.

The photovoltaic cells designed on the basis of the pn-semiconductive (semiconductor) inorganic/organic hybrid material of the invention have in particular the following advantages compared with the existing cells:

1—A greater photoconversion efficiency, in particular with regard to the photocurrent density, the photopotential and the fill factor.

2—The absence of problems linked to the presence of a liquid electrolyte, i.e. the problem of hermetically sealing the two electrodes of the cell no longer arises.

3—Compatibility of cells of this type with the production of devices on a flexible substrate (plastic, for example).

4—Possibility of using the cells in outside lighting in the presence of atmospheric moisture and where the temperature may reach 50-60° C.

5—Possibility of industrial development since all the constituents of the cell are components that are inexpensive and compatible with continuous deposition techniques (for example, roll-to-roll).

6—Possibility of using electrically conductive metal wires immersed in the conductor glass in order to drain the current in the external electric circuit.

The advantages of these cells are in particular linked to the use of the hybrid material as described above, and to the use of the complex (I) as described above.

FIG. 1 shows a photovoltaic cell according to the present invention, denoted by the overall reference 1.

The cell 1 comprises a transparent glass support 3 coated on one face 5 with a transparent conductive (conducting) layer 7, this layer possibly being based on fluorine-doped tin oxide or on ITO. The support coated with the transparent conductive (conducting) layer acts as current-collecting electrode (or "the first electrode" in the terminology employed above).

A dense titanium dioxide layer 9 is deposited on the transparent conducting layer 7. Placed on this dense layer is a layer 11 of semiconductive material, said semiconductive material corresponding to the pn-semiconductive inorganic/organic hybrid material of the invention. Deposited on this layer 11 of semiconductive material is a layer 13 of conductive polymer (this layer may optionally be omitted), on which a metal layer 15, for example a layer based on gold and/or on nickel and/or on silver and/or on aluminium, is deposited. The optional layer 13 of conductive polymer, sandwiched between the layer 11 of semiconductive material and the metal layer 15, makes it possible to limit short-circuiting. The metal layer 15 acts as counterelectrode (or "second electrode" in the terminology employed above).

FIG. 2 represents an enlarged portion of the layer 11 of semiconductive material and more precisely shows the interface between the surface of the porous oxide ceramic substrate and the complex of formula (I) according to the invention: FSEC.

In this figure, the reference 17 denotes a surface of the wall of a pore of the semiconductive porous oxide ceramic.

The surface 17 is sensitized by grafting of the compounds of formula (I) according to the invention. When a light ray reaches the chromophore substance (said light ray being represented by an arrow hv), the light energy in photon form that it transports is absorbed by the chromophore substance. The latter releases an electron e which, in this situation, is captured directly by the porous oxide ceramic, while the charge hole shown by the + symbol, created concomitantly with the electron, is captured by the conductive polymer. Thus, the electron-hole pair dissociates without recombining, therefore creating an electric current within the material.

The connection, according to the invention, via covalent bonding, between the sensitizer and the ceramic, on the one hand, and with the conducting polymer, on the other hand, allows better charge injection into the semiconductive (semiconductor) materials (ceramic and polymer).

The photovoltaic cells of the present invention may be produced in the following way:

- a deposition step, in which an oxide ceramic film is deposited on a support optionally coated with a transparent conductive layer, it being possible for said deposition to be carried out by vacuum techniques or by wet processing techniques, as described above, these two types of processes being within the understanding of the man skilled in the art;
- implementation of the process for preparing the pn-semiconductive (semiconductor) material as defined above, so as to obtain said semiconductive material from the abovementioned oxide ceramic film;
- optionally, a step of depositing, on the layer of semiconductive material, a layer of electrically conductive polymer, preferably identical to that constituting the pn-semiconductive (semiconductor) inorganic/organic hybrid material of the invention, said layer being deposited by wet processing techniques, described above, within the understanding of the man skilled in the art;
- a deposition step in which a metal layer as defined above is deposited on the layer of semiconductive material or, where appropriate, on the layer of electrically conductive polymer.

The present invention will now be described in relation to an exemplary embodiment.

Figure 1:
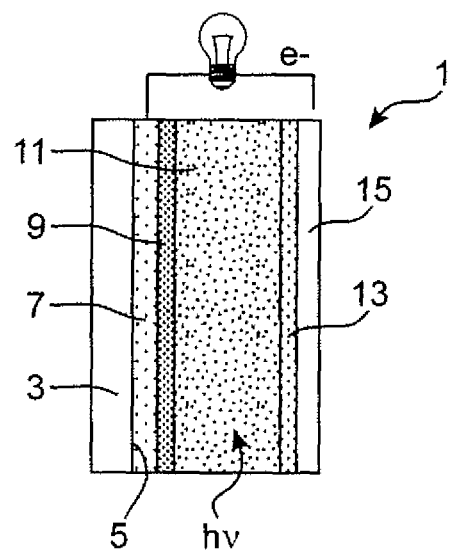
FIG. 1 corresponds to a cross sectional view of a photovoltaic cell of the invention, already described.
Figure 2:
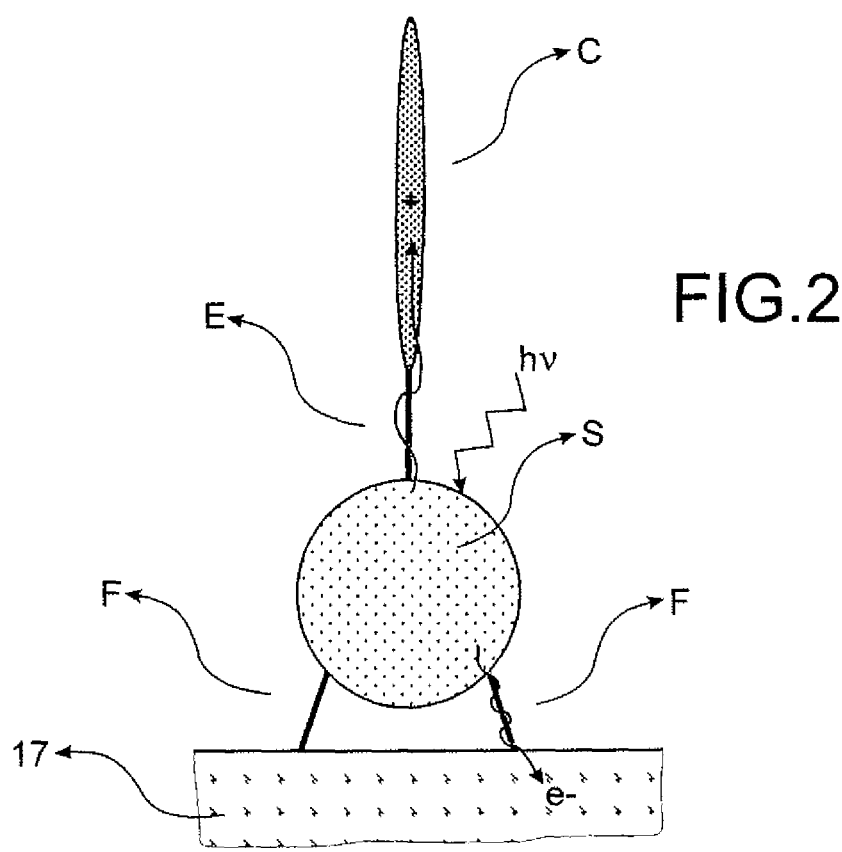
FIG. 2 corresponds to an enlargement of a portion of the cell shown in FIG. 1, this portion being described above.

The invention will now be described with reference to the examples below, given by way of nonlimiting illustration.

DETAILED DESCRIPTION OF SPECIFIC EMBODIMENTS

Example 1

Synthesis of the Complex 5 (Also Called C13)

50 mg (0.06 mmol, 1 eq.) of complex 1 as described above, dissolved in 2 mL of distilled DMF and 600 mg (0.12 mmol, 2 eq.) of polymer 2 as described above and (where R is an n-octyl group and n=40) dissolved in 10 mL of distilled THF are introduced into a sealed tube. After three rounds of degassing under argon, 9.5 mg (0.013 mmol, 0.2 eq.) of [1,1'-bis(diphenylphosphino)ferrocene]dichloropalladium (II), 2.5 mg (0.013 mmol, 0.2 eq.) of copper iodide and 0.5 mL of triethylamine are added. The mixture is heated at 90° C. for 20 hours. After cooling of the medium, the solvent is evaporated off under reduced pressure. The product obtained is purified by two successive chromatographies on alumina (column 1 eluent: methanol gradient in chloroform: from 0 to 5%, column 2 eluent: methanol gradient in chloroform: from 0 to 1%), to give a violet-black solid (70 mg, 20%).

$^1$H NMR: (300 MHz in $CDCl_3$, δ ppm)

10.56 (d, $J^3$=6 Hz, 1H), 9.06 (s, 1H), 8.78 (s, 1H), 8.39 (s, 2H), 8.29 (d, $J^3$=7.5 Hz, 2H), 7.86 (m, 3H), 7.72 (d, $J^3$=5.4 Hz, 1H), 7.51 (d, $J^3$=5.7 Hz, 2H), 7.27-7.16 (m, 3H), 6.98 (s, 38H), 4.63 and 4.39 (2q, 4H), 2.89 (m, 76H), 1.71-1.31 (m, 462H), 0.93 (t, 114H).

UV-Visible (THF, $\lambda_{max}$ in nm): 265, 303, 445, 552.

Synthesis of Intermediate 4

130 mg (0.02 mmol, 1 eq.) of complex 3 as described above, where R is an n-octyl group and n=40, dissolved in 12 mL of distilled THF, are introduced into a three-necked flask. After degassing under argon, 20 mg (0.06 mmol, 3 eq.) of palladium-on-charcoal at 20% are added before the introduction of dihydrogen. The reaction medium is stirred for 14 hours at ambient temperature. The solvent is evaporated off under reduced pressure and the crude product is purified on sephadex so as to give a violet-black solid (130 mg, quantitative).

$^1$H NMR: (300 MHz in $CDCl_3$, δ ppm)

6.98 (s, 38H), 2.89 (m, 76H), 1.71-1.31 (m, 456H), 0.93 (t, 114H).

UV-Visible (THF, $\lambda_{max}$ in nm): 265, 303, 445

Synthesis of the Complex 5

150 mg (0.02 mmol, 1 eq.) of complex 4 as described above, where R is an n-octyl group and n=40, dissolved in 10 mL of THF, 3 mL of a 0.2M solution of LiOH and 20 mg (0.6 mmol, 30 eq.) of KCN are introduced into a round-bottomed flask. After heating for 6 hours at 90° C., the solvent is evaporated off under reduced pressure. The product obtained is purified on sephadex, so as to give a violet-black solid (150 mg, quantitative) which is the complex 5, the formula of which has already been given above, where R is an n-octyl group and n=40.

¹H NMR: (300 MHz in CDCl₃, δ ppm)
6.98 (s, 38H), 2.89 (m, 76H), 1.71-1.31 (m, 456H), 0.93 (t, 114H).

UV-Visible (THF, $\lambda_{max}$ in nm): 265, 303, 445

Example 2

Synthesis of the Complex 12'

Synthesis of the 4-bromo-2,5-dimethylbenzaldehyde Intermediate 8

4 g (15 mmol, 1 eq.) of 1,4-dibromo-2,5-dimethylbenzene are solubilized in 50 mL of distilled THF, in a Schlenk tube under argon. The medium is then cooled to −78° C., then 6.6 mL (16.6 mmol, 1.1 eq.) of BuLi (2.5M in hexane) are added dropwise. After stirring at this temperature for 1 hour, 5.3 mL (68 mmol, 4.5 eq.) of freshly distilled DMF are added. The reaction medium is again stirred at this temperature for 1 hour, and then the temperature returns to ambient temperature overnight. Next, the medium is diluted with a solution of ammonium chloride and then extracted three times with ethyl acetate. The organic phases are combined, dried over magnesium sulphate, and concentrated under reduced pressure. The residue is purified by silica column chromatography (eluent: ethyl acetate/petroleum ether: 80/20), so as to give a white solid (m: 1.3 g, yield: 40%).

¹H NMR: (300 MHz in CDCl₃, δ ppm)
10.20 (s, 1H), 7.62 (s, 1H), 7.46 (s, 1H), 2.62 (s, 3H), 2.42 (s, 3H).

Synthesis of the 4'-(1-bromo-2,5-dimethyl-4-phenyl)-2,2',6',2''-terpyridine Intermediate 10

0.57 g (4.7 mmol, 2 eq.) of acetylpyridine is added to a suspension of 0.8 g (7 mmol, 3 eq.) of potassium tert-butanolate in 30 mL of distilled THF, in a three-necked flask. After stirring for 30 minutes at ambient temperature, 0.53 g (2.3 mmol, 1 eq.) of 4-bromo-2,5-dimethylbenzaldehyde is added dropwise in 5 mL of distilled THF. After stirring for 20 hours under argon, 1.8 g (23 mmol, 10 eq.) of ammonium acetate in solution in a mixture of ethanol (10 mL) and acetic acid (5 mL) are added. The reaction medium is then heated at 80° C. for 6 hours. The mixture is cooled and poured into an ice+water mixture (100 g). The precipitate that has formed is filtered off and washed with diethyl ether. The aqueous phase is extracted three times with dichloromethane. The organic phases are combined, dried over magnesium sulphate, and concentrated under reduced pressure. The residue and the precipitate are combined and purified by alumina column chromatography (deposition solid, eluent: ethyl acetate gradient in petroleum ether: from 0 to 30%), so as to give a white solid (m: 350 mg, yield: 36%).

¹H NMR: (300 MHz in CDCl₃, δ ppm)
8.70 (d, J³=3.9 Hz, 2H), 8.67 (d, J³=7.8 Hz, 2H), 7.88 (dd, J⁴=1.2 Hz, J³=7.8 Hz, J³=7.8 Hz, 2H), 7.48 (s, 1H), 7.34 (ddd, J⁴=1 Hz, J³=4.8 Hz, J³=7.8 Hz, 2H) 7.24 (s, 1H), 2.40 (s, 3H), 2.31 (s, 3H).

Synthesis of Intermediate 12

60 mg (0.14 mmol, 1 eq.) of 4'-(1-bromo-2,5-dimethyl-4-phenyl)-2,2',6',2''-terpyridine solubilized in a minimum amount of THF, 159 mg (0.26 mmol, 1.8 eq.) of dichlorobis(dimethyl sulphoxide)(diethyl-2,2'-bipyridine 4,4'-dicarboxylate)ruthenium (II) solubilized in 8 mL of ethanol and 30 mg (0.72 mmol, 5 eq.) of lithium chloride dissolved in 0.5 mL of H₂O are introduced into a 25 mL round-bottomed flask. The mixture is heated at the reflux of ethanol for 16 hours. After cooling of the medium, the solvent is evaporated off under reduced pressure. The product obtained is solubilized in a minimum amount of acetone and then the addition of a saturated solution of sodium tetrafluoroborate results in precipitation of a pink solid, which is isolated by filtration. The product obtained is again solubilized in a minimum amount of dichloromethane and acetone and then precipitated by adding diethyl ether, so as to give a pink solid (61 mg, 45%).

¹H NMR: (300 MHz in CDCl₃, δ ppm)
10.6 (d, J³=5.7 Hz, 2H), 9.04 (s, 2H), 8.74 (s, 2H), 8.37 (d, J³=4.8 Hz, H), 8.31 (s, 2H), 8.26 (d, J³=8.1 Hz, 2H), 7.92 (d, J³=5.7 Hz, 2H), 7.83 (m, 3H), 7.61 (s, 1H), 7.48 (m, 3H), 7.17 (t, J³ and J³=5.8 Hz, 2H), 4.64 (q, 2H), 4.35 (q, 2H), 2.46 and 2.44 (2s, 6H), 1.51 (t, 3H), 1.31 (t, 3H).

Synthesis of the Complex 12'

1 mL of a 4M solution of lithium hydroxide is added to 9 mg of complex 12 and 3 mg of potassium cyanide dissolved in 3 mL of DMF, in a 25 mL round-bottomed flask. The reaction medium is heated at 120° C. for 16 hours. After a return to ambient temperature, the addition of diethyl ether causes precipitation of an orange solid. The product is filtered off, solubilized in a minimum amount of methanol and then reprecipitated by adding a few drops of HBF₄ and then water. The product is purified on Sephadex®, so as to give an orange solid (m: 7.7 mg, yield: 86%).

¹H NMR: (300 MHz in MeOD, δ ppm)
10.3 (d, J³=5.7 Hz, 2H), 9.04 (s, 2H), 8.74 (s, 2H), 8.37 (d, J³=4.8 Hz, 1H), 8.31 (s, 2H), 8.26 (d, J³=8.1 Hz, 2H), 7.92 (d, J³=5.7 Hz, 2H), 7.83 (m, 3H), 7.61 (s, 1H), 7.84 (m, 3H), 7.17 (t, J³ and J³=5.8 Hz, 2H), 2.46 and 2.44 (2s, 6H).

UV-Visible (THF, $\lambda_{max}$ in nm): 283, 305, 495

Example 3

Synthesis of the Complex C3 of Formula Below (4'-phosphonic-2,2':6',2''-terpyridine)(4'-[(3',4'-dioctyl-2,2':5',2''-terthiophen)-5-yl]-2,2':6',2''-terpyridine)ruthenium(II) acid ditetrafluoroborate

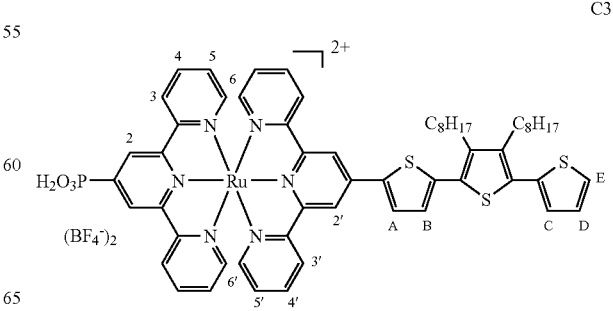

C3

Synthesis of the intermediate complex C3a: 4'-[(3',4'-dioctyl-2,2':5',2''-terthiophene)-5-yl]-2,2':6',2''-terpyridine Synthesis of the Intermediate Complex C3b 4'-diethoxyphosphonate-2,2':6',2''-terpyridine)(4'-[(3',4'-dioctyl-2,2':5',2''-terthiophen)-5-yl]-2,2':6',2''-terpyridine)ruthenium(II) ditetrafluoroborate (17)

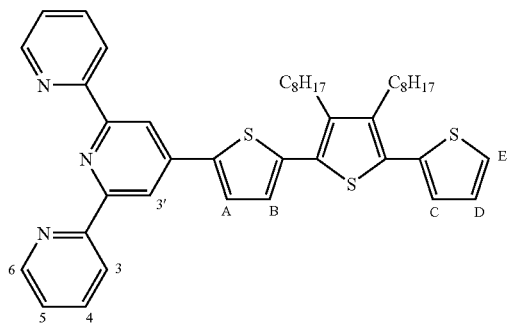

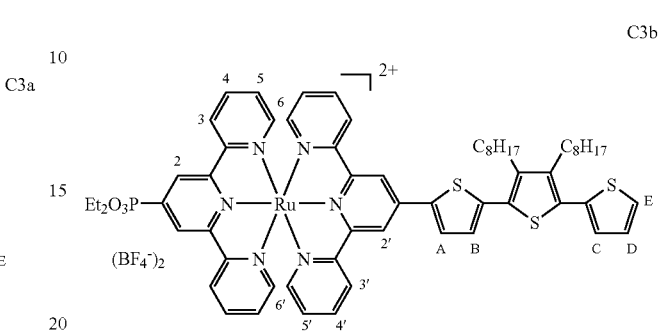

100 mg (0.25 mmol, 1 eq.) of 4'-trimethylstannyl-2,2':6',2''-terpyridine, 200 mg (0.38 mmol, 1.2 eq.) of 5-bromo-3',4'-dioctyl-2,2':5',2''-terthiophene and 15 mL of distilled dioxane are introduced into a sealed tube. After three rounds of degassing under argon, 26 mg (0.025 mmol, 0.045 eq.) of tris(dibenzylideneacetone)dipalladium, 85 mg (0.55 mmol, 2.2 eq.) of caesium fluoride and 18 mg (0.09 mmol, 0.18 eq.) of tri-tert-butylphosphine are added. The mixture is heated at 130° C. for 16 hours. After cooling of the medium, the solution is diluted with ethyl acetate, and washed with a dilute solution of ammonia and with water. The organic phase is dried over magnesium sulphate, filtered, and then concentrated under vacuum. The product obtained is purified by silica chromatography (eluent: gradient of diethyl ether in dichloromethane (from 0 to 40%)), so as to give an orange solid (143 mg, 80%).

$^1$H NMR: (300 MHz in CDCl$_3$, δ ppm)
8.74 (d, $^3J_{6-5}$=4.8 Hz, 2H, H$_5$), 8.68 (s, 2H, H$_{3'}$), 8.62 (d, $^3J_{3-4}$=7.8 Hz, 2H, H$_3$), 7.88 (ddd, J$_{4-3}$=7.8 Hz, J$_{4-5}$=7.8 Hz, J$_{4-6}$=1.8 Hz, 2H, H$_4$), 7.74 (d, $^3J_{A-B}$=3.9 Hz, 1H, H$_A$), 7.37 (ddd, $^3J_{5-4}$=7.8 Hz, $^3J_{5-6}$=4.8 Hz, $^4J_{5-3}$=1.8 Hz, 2H, H$_5$), 7.33 (dd, $^3J_{E-D}$=5.1 Hz, $^3J_{D-C}$=3.6, $^3J_{E-C}$=1.2 Hz, 1H, H$_E$), 7.19 (d, $^3J_{B-A}$=3.9 Hz, 1H, H$_B$), 7.17 (dd, $^3J_{C-D}$=3.6 Hz, $^3J_{C-E}$=1.2 Hz, 1H, H$_C$), 7.07 (dd, $^3J_{D-E}$=5.1 Hz, 1H, H$_D$), 2.78 (t, 4H CH$_2$ alk at α), 2.71 (t, 4H, CH$_2$ alk at β), 1.28-1.62 (m, 30H, CH$_2$ alk), 0.87 (m, 6H, CH$_3$ alk).

$^{13}$C NMR: (300 MHz in CDCl$_3$, δ ppm)
14.1; 22.6; 28.1; 29.3; 29.9; 30.6; 30.7; 31.9; 116.7; 121.3; 123.8; 125.4; 125.9; 126.2; 126.6; 127.4; 129.5; 130.4; 136.1; 136.8; 138.2; 140.3; 140.7; 140.9; 143.1; 149.1; 156.0.

0.16 mmol, 1.1 eq., of (4'-diethoxyphosphoryl-2,2':6',2''-terpyridine)ruthenium(III) trichloride and 91 mg (0.47 mmol, 3.3 eq.) of silver tetrafluoroborate are heated at 60° C. for 1 h30 in a degassed mixture of ethanol (20 mL) and distilled DMF (5 mL). After cooling of the medium, the solution is filtered in order to remove the silver chloride that has formed. The filtrate is degassed and again introduced into a reaction with a solution of 91 mg (0.14 mmol, 1 eq.) of 4'-[(3',4'-dioctyl-2,2':5,2''-terthiophen)-5-yl]-2,2':6,2''-terpyridine and 60 mg (0.56 mmol, 4 eq.) (C3a) of hydroquinone in 4 mL of distilled DMF. The reaction medium is refluxed for 5 hours. The addition of diethyl ether results in the precipitation of a solid, which is filtered off, washed with diethyl ether and dried under vacuum. The product obtained is purified by silica chromatography (eluent: gradient of water and of a solution of KNO$_3$ in acetone (from 90:10:0 to 70:20:1 acetone/H$_2$O/KNO$_3$)), so as to give a red solid. The complex is dissolved in a minimum amount of methanol and precipitated by adding a saturated solution of NaBF$_4$, so as to give a red solid (105 mg, 60%).

$^1$H NMR: (300 MHz in CDCl$_3$, αppm)
8.90 (d, 2H, $^3J_{2-P}$=13 Hz, H$_2$), 8.86 (s, 2H, H$_{2'}$), 8.60 and 8.47 (2d, 4H, $^3J_{3-4}$ and $^3J_{3'-4'}$=7.8 Hz, H$_3$ and H$_{3'}$), 8.16 (d, 1H, $^3J_{A-B}$=3.3 Hz, H$_A$), 7.82 (m, 4H, H$_4$ and H$_{4'}$), 7.49 and 7.32 (2d, 4H, $^3J_{6-5}$) and $^3J_{6'-5'}$=5.2 Hz, H$_6$ and H$_{6'}$), 7.41 (dd, 1H, $^3J_{E-D}$=4.8 Hz, $^4J_{E-C}$=1.5 Hz, H$_E$), 7.24 (m, 2H, H$_B$ and H$_C$), 7.14 (m, 4H, H$_5$ and H$_{5'}$), 6.81 (m, 1H, H$_D$), 4.48 (q, 4H, OCH$_2$CH$_3$), 2.77 (t, 4H CH$_2$ alk at α), 2.68 (t, 4H, CH$_2$ alk at β), 1.25-1.67 (m, 30H, OCH$_2$CH$_3$ and CH$_2$ alk), 0.88 (m, 6H, CH$_3$ alk).

$^{13}$C NMR: (300 MHz in CDCl$_3$, δ ppm)
14.08; 16.52; 22.67; 29.26; 29.31; 29.68; 29.91; 29.98; 30.84; 31.90; 64.24; 119.16; 119.50; 124.95; 125.23; 127.51; 127.69; 128.01; 128.15; 128.25; 128.58; 129.80; 130.84; 131.31; 133.67; 137.84; 138.08; 138.36; 140.55; 140.68; 140.88; 141.67; 145.89; 151.91; 152.64; 154.65; 155.39; 157.45; 157.51.

Final Synthesis of the Complex C3:
70 mg (0.05 mmol, 1 eq.) of complex C3b are introduced, in a sealed tube, into 10 mL of freshly distilled DMF and 400 mg (2.5 mmol, 35 eq.) of anhydrous bromotrimethylsilane are then carefully added under argon. The reaction medium is heated at 50° C. for 36 hours under argon. After a return to ambient temperature, the addition of dichloromethane results in the precipitation of a solid, which is filtered off, washed with dichloromethane, and dried under vacuum. The complex is dissolved in a minimum amount of methanol and precipitated by adding a saturated solution of NaBF$_4$, so as to give a red solid which is purified on a Sephadex column (65 mg, 90%).

$^1$H NMR: (300 MHz in CDCl$_3$/MeOD (90/10), δ ppm)
9.10 (d, 2H, $^3J_{2-P}$=13 Hz, H$_2$), 8.81 (s, 2H, H$_{2'}$), 8.58 (d, 4H, $^3J_{3-4}$ and $^3J_{3'-4'}$=8.4 Hz, H$_3$ and H$_{3'}$), 8.19 (d, 1H, $^3J_{A-B}$=3.6 Hz, H$_A$), 7.88 (m, 4H, H$_4$ and H$_{4'}$), 7.28 (m, 5H, H$_6$, H$_{6'}$ and H$_E$), 7.20-7.00 (m, 7H, H$_B$, H$_C$, H$_5$, H$_{5'}$ and H$_D$), 2.77 (t, 4H, CH$_2$ alk at α), 2.68 (t, 4H, CH$_2$ alk at β), 1.25-1.58 (m, 26H, CH$_2$ alk), 0.80 (m, 6H, CH$_3$ alk).

$^{13}$C NMR: (300 MHz in CDCl$_3$/MeOD (90/10), δ ppm)
13.51; 22.24; 27.70; 28.80; 28.89; 29.21; 29.43; 29.45; 30.30; 30.35; 31.47; 118.52; 124.39; 124.43; 125.59; 125.92; 127.15; 127.48; 127.66; 128.22; 129.29; 131.10; 131.19; 135.13; 137.49; 138.07; 140.05; 140.72; 141.35; 141.90; 144.95; 151.27; 151.68; 154.69; 157.40; 157.78.

Example 4

Synthesis of the Complex C4

Ruthenium(II) [4'-(2-(3',4'-dioctyl-2,2':5',2"-terthiophen-5-yl)ethyl)-2,2':6',2"-terpyridine]-2,2':6',2"-terpyridine-4'-phosphonic acid bis(tetrafluoroborate) (C4)

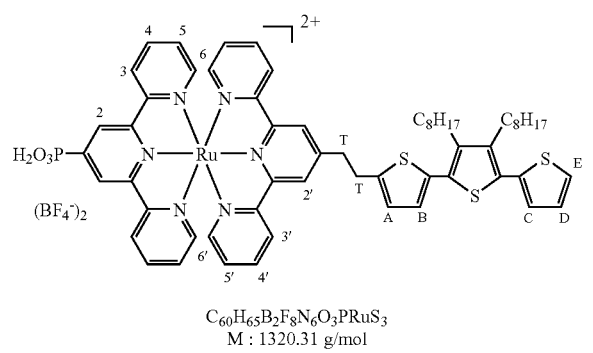

C$_{60}$H$_{65}$B$_2$F$_8$N$_6$O$_3$PRuS$_3$
M : 1320.31 g/mol

Synthesis of the Intermediate Complex C4a

Ruthenium(II) [4'-((3',4'-dioctyl-2,2':5',2"-terthiophen-5-yl)ethynyl)-2,2':6',2"-terpyridine]-2,2':6', 2"-terpyridine-4'-diéthylphosphonate bis-tetrafluoroborate

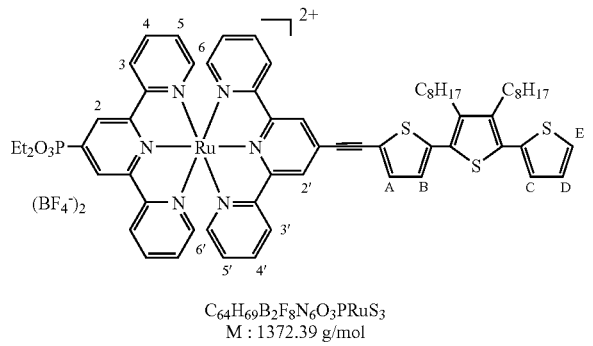

C$_{64}$H$_{69}$B$_2$F$_8$N$_6$O$_3$PRuS$_3$
M : 1372.39 g/mol 98 mg (0.2 mmol, 2 eq.) of 5-(ethynyl)-3',4'-dioctyl-2,2': 5',2"-terthiophene, 1 mL of distilled triethylamine and 6.5 mL of distilled DMF are introduced into a sealed tube. After three rounds of degassing under argon, 15 mg (0.02 mmol, 0.2 eq.) of [1,1'-bis(diphenylphosphino)ferrocene]dichloropalladium and 4 mg (0.02 mmol, 0.2 eq.) of copper iodide and 96 mg (0.1 mmol, 1 eq.) of [4'-bromo-2,2':6',2"-terpyridine][4'diethoxyphosphoryl-2,2':6',2"-terpyridine]ruthenium(II) bis(tetrafluoroborate) are added. The mixture is heated at 90° C. for 16 hours. After cooling of the medium, the addition of a saturated solution of sodium tetrafluoroborate causes a red solid to precipitate, which solid is filtered off. The product obtained is purified by silica chromatography (eluent: gradient of water and of a solution of KNO$_3$ in acetonitrile (from 100:0:0 to 70:20:1 acetone/H$_2$O/KNO$_3$)), so as to give a red solid. The complex is dissolved in a minimum amount of methanol and precipitated by adding a saturated solution of NaBF$_4$, so as to give a red solid (m: 50 mg, yield: 40%).

$^1$H NMR: (300 MHz in CD$_3$CN, δ ppm)
9.0 (d, $^3J_{2-P}$=13.5 Hz, 2H, H$_2$), 8.93 (s, 2H, H$_{2'}$), 8.72 and 8.57 (2d, $^3J_{3-4}$ and $^3J_{3'-4'}$=7.8 Hz, 4H, H$_3$ and H$_{3'}$), 7.97 (m, 4H, H$_4$ and H$_{4'}$), 6.65 (d, $^3J_{E-D}$=3.9 Hz, 1H, H$_E$), 7.49 and 7.38 (m, 4H, H$_6$ and H$_{6'}$), 7.30-7.15 (m, 8H, H$_4$, H$_B$, H$_C$, H$_D$, H$_5$ and H$_{5'}$), 4.42 (m, 4H, OCH$_2$CH$_3$), 2.77 (t, 4H CH$_2$ alk at α), 2.68 (t, 4H, CH$_2$ alk at β), 1.25-1.67 (m, 26H, OCH$_2$CH$_3$ and CH$_2$ alk), 0.88 (m, 6H, CH$_3$ alk).

$^{13}$C NMR: (300 MHz in CD$_3$CN, δ ppm)
158.3; 156.6; 156.5; 155.9; 153.8; 153.4; 142.7; 141.6; 141.4; 139.4; 139.3; 132.1; 132.2; 129.4; 128.9; 128.7; 127.4; 126.1; 126.0; 125.7; 92.5; 91.4; 32.6; 31.3; 30.4; 29.9; 29.0; 23.4; 16.9; 16.8; 14.4.

Synthesis of the Intermediate Complex C4b

Ruthenium(II) [4'-(2-(3',4'-dioctyl-2,2':5',2"-terthiophen-5-yl)ethyl)-2,2':6',2"-terpyridine]-2,2':6',2"-terpyridine-4'-diethylphosphonate bis(tetrafluoroborate)

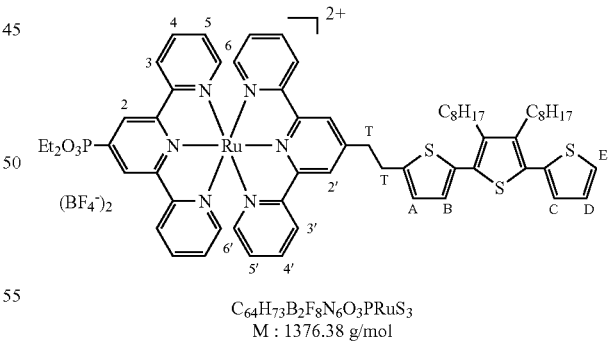

C$_{64}$H$_{73}$B$_2$F$_8$N$_6$O$_3$PRuS$_3$
M : 1376.38 g/mol 80 mg (0.06 mmol, 1 eq.) of complex C4a in 12 mL of distilled methanol are introduced into a three-necked flask. After degassing under argon, 40 mg (0.06 mmol, 3 eq.) of palladium-on-charcoal at 20% are added, before the introduction of dihydrogen. The reaction medium is stirred vigorously for 14 hours at ambient temperature. The medium is filtered over celite and then the solvent is evaporated off under reduced pressure. The residue is purified on Sephadex LH20, so as to give an orangey-red solid (m: 56 mg, yield: 70%).

$^1$H NMR: (300 MHz in $CD_3CN$+1 drop of MeOD, δ ppm) 8.93 (d, $^3J_{2\text{-}P}$=13.5 Hz, 2H, $H_2$), 8.62 (d, $^3J_{3\text{-}4}$=7.8 Hz, 2H, $H_3$), 8.57 (s, 2H, $H_{2'}$), 8.40 (d, $^3J_{3'\text{-}4'}$=7.8 Hz, 4H, $H_{3'}$), 7.88 (m, 4H, $H_4$ and $H_{4'}$), 7.41 (d, $^3J_{E\text{-}D}$=3.9 Hz, 1H, $H_E$), 7.31 and 7.27 (m, 4H, $H_6$ and $H_{6'}$), 7.13-7.00 (m, 8H, $H_A$, $H_B$, $H_C$, $H_D$, $H_5$ and $H_{5'}$), 4.42 (m, 4H, $OCH_2CH_3$), 3.5 (m, 4H, $2CH_{2T}$), 2.77 (t, 4H, $CH_2$ alk at α), 2.68 (t, 4H, $CH_2$ alk at β), 1.25-1.67 (m, 26H, $OCH_2CH_3$ and $CH_2$ alk), 0.88 (m, 6H, $CH_3$ alk).

$^{13}$C NMR: (300 MHz in $CD_3CN$+1 drop of MeOD, δ ppm) 158.6; 158.3; 156.5; 155.0; 153.6; 152.8; 144.2; 141.0; 139.1; 138.8; 128.5; 128.1; 127.4; 127.0; 126.7; 125.8; 125.1; 64.4; 38.2; 32.3; 31.1; 30.1; 29.7; 28.4; 23.1; 16.9; 16.8; 14.2.

Final Synthesis of the Complex C4

50 mg (0.36 mmol, 1 eq.) of complex C4b are introduced, in a sealed tube, into 3 mL of freshly distilled DMF, and 290 mg (2 mmol, 50 eq.) of anhydrous bromotrimethylsilane are then carefully added under argon. The reaction medium is heated at 50° C. for 36 hours under argon. After a return to ambient temperature, the addition of dichloromethane results in the precipitation of a solid, which is filtered off, washed with dichloromethane, and dried under vacuum. The complex is dissolved in a minimum amount of methanol and precipitated by adding a saturated solution of $NaBF_4$, so as to give a red solid which is purified on a Sephadex LH20 column (m: 40 mg, yield: 90%).

$^1$H NMR: (300 MHz in MeOD+1 drop of $CD_3CN$, δ ppm) 9.16 (d, 2H, $^3J_{2\text{-}P}$=13.5 Hz, $H_2$), 8.67 (d, 2H, $^3J_{3\text{-}4}$=7.8 Hz, $H_3$), 8.57 (s, 2H, $H_{2'}$), 8.40 (d, 4H, $^3J_{3'\text{-}4'}$=7.8 Hz, $H_{3'}$); 7.83 (m, 4H, $H_4$ and $H_{4'}$), 7.39 (d, $^3J_{E\text{-}D}$=3.9 Hz, 1H, $H_E$), 7.33 and 7.27 (m, 4H, $H_6$ and $H_{6'}$), 7.13-7.00 (m, 8H, $H_A$, $H_B$, $H_C$, $H_D$, $H_5$ and $H_{5'}$), 3.5 (m, 4H, $2CH_{2T}$), 2.77 (t, 4H $CH_2$ alk at α), 2.68 (t, 4H, $CH_2$ alk at β), 1.25-1.67 (m, 20H, $CH_2$ alk), 0.88 (m, 6H, $CH_3$ alk).

Example 5

Manufacture of Photovoltaic Cells

A conducting glass plate (fluorine-doped $SnO_2$), on which a dense $TiO_2$ layer has been deposited, is washed with water, rinsed with acetone and with ethanol, and then dried under a stream of nitrogen. A transparent film of $TiO_2$ nanoparticles is then deposited by spin coating with a solution of titanium dioxide provided by the company Solaronix. After drying for 5 minutes in ambient air, the substrate is heated at 450° C. for 30 minutes. The thickness of the $TiO_2$ film obtained is approximately 1.5 μm.

The plate is immersed in a solution of dye, complex (conditions in the following table) for 16 hours before being rinsed with the same solvent, and dried.

| dye | solvent | concentration | temperature |
|---|---|---|---|
| 5 | THF | $2 \times 10^{-3}$M | 60° C. |
| 12' | EtOH/MeOH (90/10) | $3 \times 10^{-4}$M | 25° C. |

Next, a solution at 35 g·L$^{-1}$ of poly(3-octylthiophene) in toluene is deposited by spin coating. To finish, the cell is coated with a layer of gold of 200 nm deposited by PVD.

Photovoltaic cells are prepared in a similar manner, with the other complexes prepared above and the other tested dyes, complexes, mentioned.

Example 6

Performances of the Photovoltaic Cells Comprising Complexes 5 and 12'

The results of the photovoltaic performances of the dry cells based on the dyes 12' and on the complexes 5 are given in table 1 below.

TABLE 1

| Complex | *Voc (V) | *Isc (mA.cm$^2$) | *ff (%) | *η (%) |
|---|---|---|---|---|
| 5 | 0.71 | 0.53 | 60 | 0.22 |
| 12' | 0.68 | 0.30 | 26 | 0.05 |

*Mean of five independent measurements,
Voc = open-circuit voltage,
Isc = short-circuit current and
ff = fill factor.

These measurements clearly show that the use, in photovoltaic cells, of a dying complex which comprises a chemical link between the sensitizing group and the conductive polymer chain, as is the case in the complex 5 in accordance with the invention, makes it possible to quadruple the efficiency of the photovoltaic cell compared with a photovoltaic cell in which a complex-dye not in accordance with the invention and not comprising such a chemical link, for instance a spacer, between the sensitizer group and the conducting polymer, is used.

All three of the output current, the photopotential and the fill factor are enhanced by using the complex and the new hybrid material according to the invention.

In examples 7 and 8 which follow, the performances of photovoltaic cells comprising compounds C1, C3 and C4, which are bisterpyridine-type sensitizers, and compounds C9, C12 and C13 (compound 5 of example 1), which are bipyridine terpyridine-type sensitizers, are described.

Compounds C1 and C9 are used, for comparison, as non-grafted analogues of compounds "C3 and C4" and "C12 and C13", respectively. Compounds C3 and C12 do not comprise a spacer, while compounds C4 and C13 comprise a spacer and are therefore in accordance with the invention.

Example 7

Performance of the Photovoltaic Cells Comprising Bisterpyridine-Type Sensitizer Complexes: Namely Compounds C1, C3 and C4 (27)

| Compounds | Reference | Voc | Isc | ff | η |
|---|---|---|---|---|---|
| 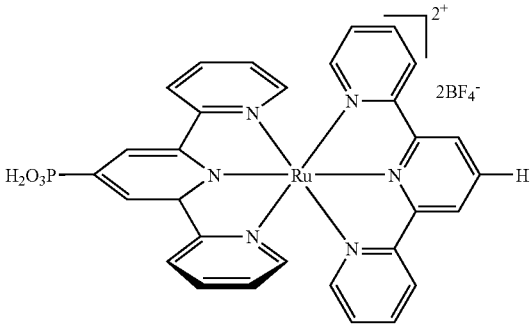 | C1 | 0.7 | 0.15 | 35 | 0.04 |
| 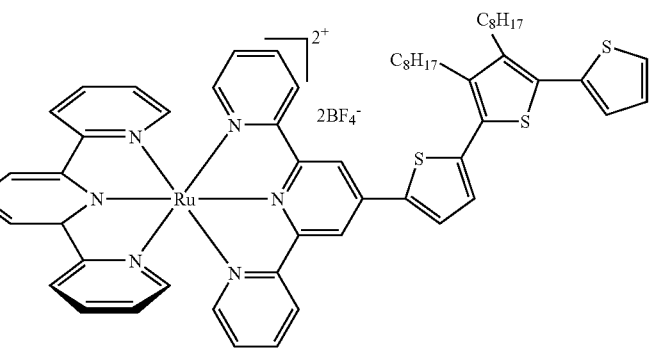 | C3 | 0.78 | 0.13 | 33 | 0.035 |
| 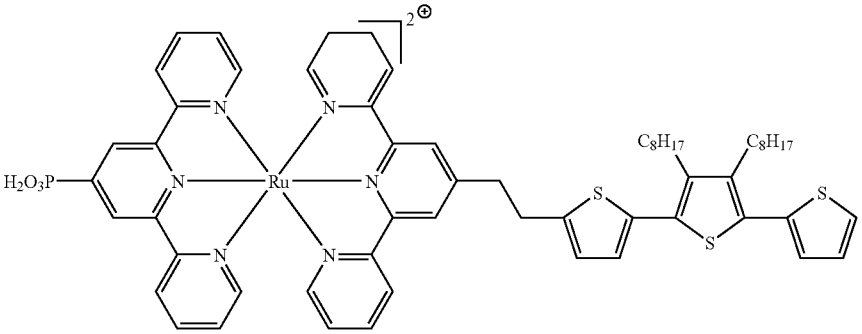 | C4 | 0.95 | 0.14 | 35 | 0.05 |

C1 is a reference dye used to produce cells according to the conventional technique, i.e. deposition of polymer by spin coating.
Complex C3, on which a polythiophene oligomer is grafted without spacer, as described in document [31], produces a decrease in efficiency of 12.5% compared with C1.
Complex C4 in accordance with the invention, on which the polythiophene oligomer is grafted using a spacer, produces an increase in efficiency of 25% compared with C1.

Example 8

Performance of Photovoltaic Cells Comprising Bipyridine Terpyridine-Type Sensitizer Complexes

| Compounds | Reference | Voc | Isc | ff | η |
|---|---|---|---|---|---|
| [structure with HOOC-bipyridine-Ru(CN)(CN)-terpyridine-phenyl-CH″] | C9 | 0.58 | 0.34 | 64 | 0.13 |
| [structure with HOOC-bipyridine-Ru(CN)(CN)-terpyridine-(EDOT)₂] | C12 | 0.77 | 0.27 | 33 | 0.068 |
| [structure with HOOC-bipyridine-Ru(CN)(CN)-terpyridine-(thiophene-R)₂-H, cationic] | C13 (5) (n = 40 and R = n-octyl) | 0.79 | 0.51 | 66 | 0.27 |

The sensitizer C9 is a reference dye used to produce cells according to the conventional technique, i.e. deposition of polymer by spin coating.
Complex C12, on which a polythiophene oligomer is grafted without spacer, as described in document [31], produces a decrease in efficiency of 47.7% compared with C9.
Complex C13 (5) in accordance with the invention, on which the polythiophene oligomer is grafted using a spacer, produces an increase in efficiency of 107.6% compared with C9.

The following remarks may be made with regard to examples 7 and 8:

C3 and C12 do not have a spacer. The photovoltaic results for these materials are inferior to those of their non-grafted homologues. This shows that direct grafting is detrimental, contrary to what is expressed in document [31].

C4 and C13 (5) have a spacer. The photovoltaic results for these materials are superior to those of their non-grafted homologues, thereby showing the advantage of grafting with a spacer.

The invention claimed is:

1. A complex of formula (I)

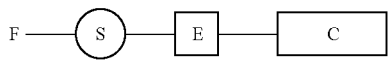

in which:
- F represents one or more groups capable of grafting chemically to a substrate of semiconductive porous oxide ceramic;
- S represents a sensitizing group for the semiconductive porous oxide ceramic;
- C is an electrically conductive polymer;
- E is a deconjugating spacer group which makes it possible to electrically isolate the sensitizer (S) from the electrically conductive polymer (C).

2. The complex according to claim 1, in which said semiconductive porous oxide ceramic is an n-type or p-type semiconductive ceramic with a wide band gap.

3. The complex according to claim 1, in which the group(s) F capable of grafting chemically to the semiconductive porous oxide ceramic is (are):
- COOR$^1$ with R$^1$ representing a hydrogen atom, an alkyl group comprising from 1 to 30 carbon atoms or a phenyl group;
- COCl;
- COCH$_2$CO—R$^1$ with R$^1$ representing a hydrogen atom, an alkyl group comprising from 1 to 30 carbon atoms or a phenyl group;
- PO(OH)$_2$, —PO(OR$^2$)(OH) or —PO(OR$^2$)(OR$^3$) with R$^2$ and R$^3$, which may be identical or different, representing an alkyl group comprising from 1 to 30 carbon atoms or a phenyl group;
- CO(NHOH);
- M(OR$^4$)$_{m-x}$Z$_x$ with x being an integer ranging from 1 to (m−1), M being a metal or a metalloid, m being an oxidation number of M, R$^4$ representing a hydrogen atom, an alkyl group comprising from 1 to 30 carbon atoms, a phenyl group, a monovalent metal cation or a group of formula N$^+$R$^1_4$, with R$^1$ representing a hydrogen atom, an alkyl group comprising from 1 to 30 carbon atoms, or a phenyl group, and Z represents a hydrogen atom, an alkyl group comprising from 1 to 30 carbon atoms, a phenyl group or a halogen atom;
- SO$_3$M' with M' representing a hydrogen atom, a monovalent metal cation or a group of formula N$^+$R$^1_4$ with R$^1$ representing a hydrogen atom, an alkyl group comprising from 1 to 30 carbon atoms or a phenyl group;
- B(OM')$_2$ with M' representing a hydrogen atom, a monovalent metal cation or a group of formula N$^+$R$^1_4$ with R$^1$ representing a hydrogen atom, an alkyl group comprising from 1 to 30 carbon atoms or a phenyl group;
- OH;

and combinations thereof.

4. The complex according to claim 1, in which said sensitizing group S is chosen from polypyridine complexes with a transition metal and organic cations.

5. The complex according to claim 4, in which said sensitizing group is a group of formula:

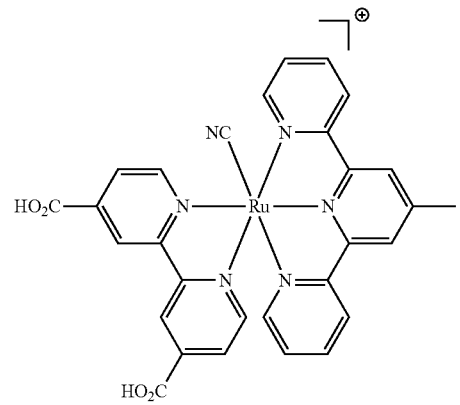

Formula (II)

or of formula

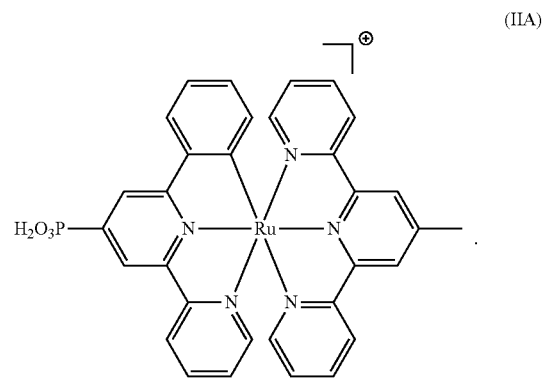

(IIA)

6. The complex according to claim 1, in which said electrically conductive polymer C is chosen from poly(acetylene)s, poly(p-phenylene)s, poly(p-phenylene vinylene)s, poly(p-phenylene sulphide)s, poly(pyrrole)s, poly(thiophene)s, poly(alkylthiophene)s, poly(dialkylthiophene)s, poly(furan)s, poly(alkoxythiophene)s, poly(azulene)s, poly(azine)s, poly(aniline)s, poly(cyanophenylene vinylene)s, poly(para-pyridyl vinylene)s, and poly(dioxythiophene)s ("PEDOT"), and blends and/or combinations and/or copolymers thereof.

7. The complex according to claim 6, in which said electrically conductive polymer C is a regioregular polymer.

8. The complex according to claim 7, in which said electrically conductive polymer is chosen from the following polymers:

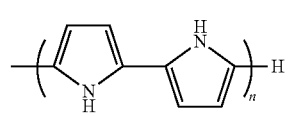

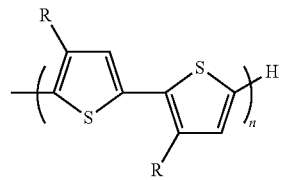

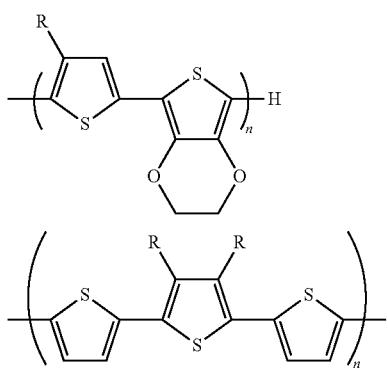

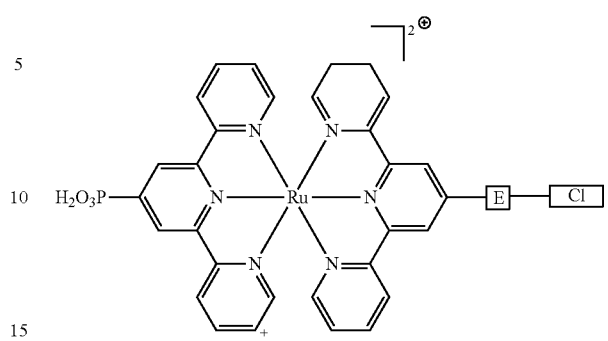

where n represents an integer from 1 to 1000, and R represents a group chosen from alkyl groups having from 1 to 24 carbon atoms, and alkoxy groups having from 1 to 24 carbon atoms.

9. The complex according to claim 1, in which the deconjugating spacer group E is chosen from the groups:

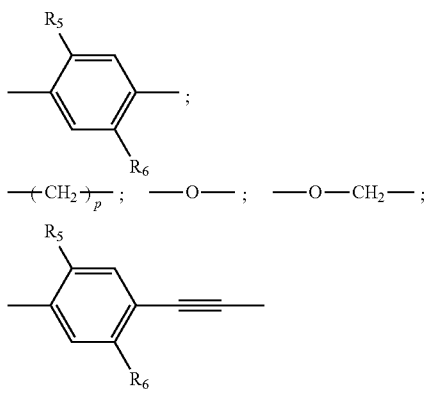

where $R_5$ and $R_6$, which may be identical or different, are chosen from alkyl groups having from 1 to 24 carbon atoms, and alkoxy groups having from 1 to 24 carbon atoms; and wherein p is an integer from 1 to 20.

10. The complex according to claim 1, which corresponds to formula (III) or (IIIA) below:

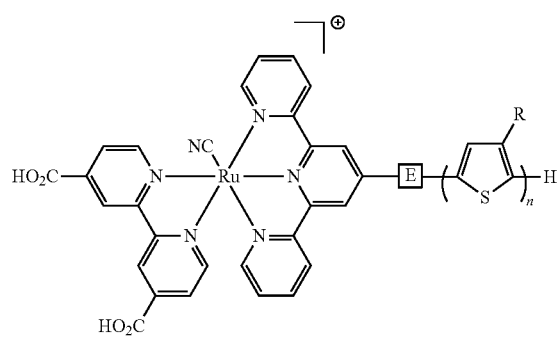

in which n represents an integer from 1 to 1000; R represents an alkyl group having from 1 to 24 carbon atoms, or an alkoxy group having from 1 to 24 carbon atoms; and E is chosen from the groups

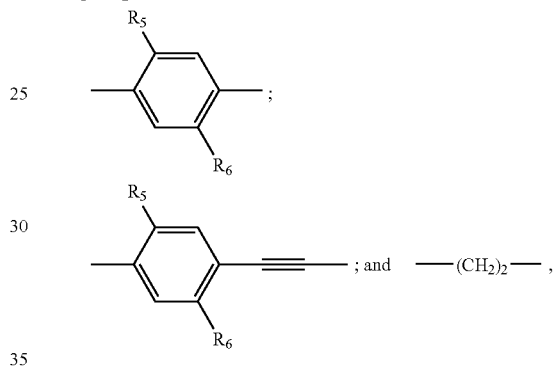

$R_5$ and $R_6$, which may be identical or different, are chosen from alkyl groups having from 1 to 24 carbon atoms, and alkoxy groups having from 1 to 24 carbon atoms; and C1 represents:

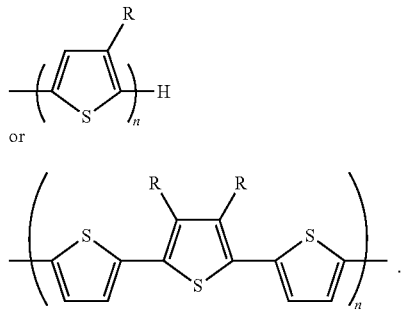

11. A process for preparing a complex of formula (III) according to claim 10, where E represents —(CH$_2$)$_2$—, or

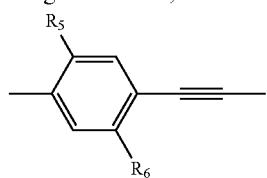

in which the following successive steps are carried out:
a)—a compound of formula 1 below, or a compound of formula 12 below:

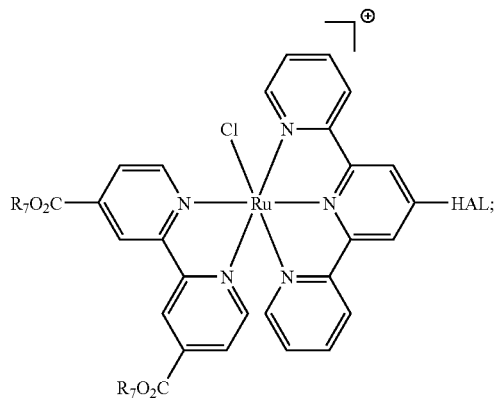

1

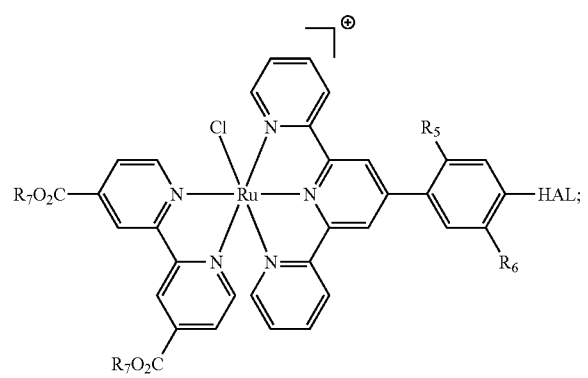

12 is reacted with a compound of formula 2 below:

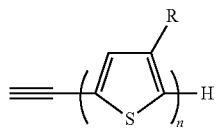

2 in which n represents an integer from 1 to 1000, and R, $R_5$, $R_6$ and $R_7$, which may be identical or different, represent an alkyl group having from 1 to 24 carbon atoms or an alkoxy group having from 1 to 24 carbon atoms, and HAL represents a halogen atom; according to a SONOGASHIRA reaction, in a mixture of DMF/THF, in the presence of a catalytic system comprising copper iodide, [1,1'-bis(diphenylphosphino)ferrocene]dichloropalladium(II) and triethylamine, so as to obtain respectively a compound of formula 3 below, or a compound of formula 13 below:

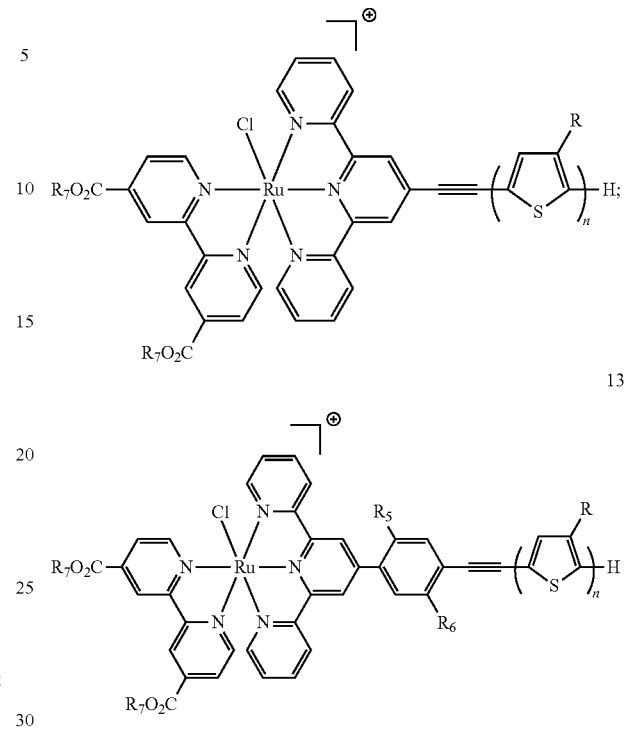

b)—the compound of formula 3 is reacted with hydrogen in THF in the presence of palladium-on-charcoal, so as to obtain a compound of formula 4 below:

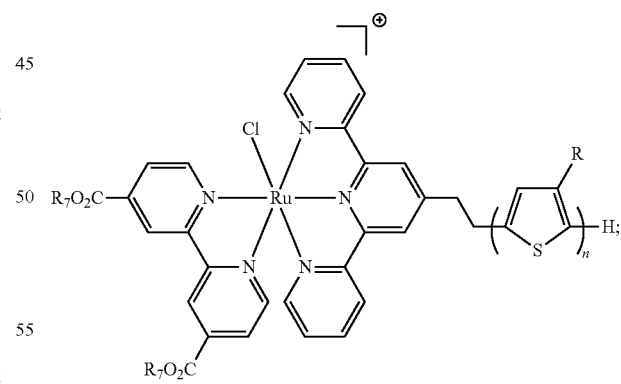

c)—the compound of formula 4 or the compound of formula 13 is reacted, in a mixture of THF/$H_2O$, with KCN/LiOH, so as to obtain respectively a compound of formula 5 below or of formula 14 below:

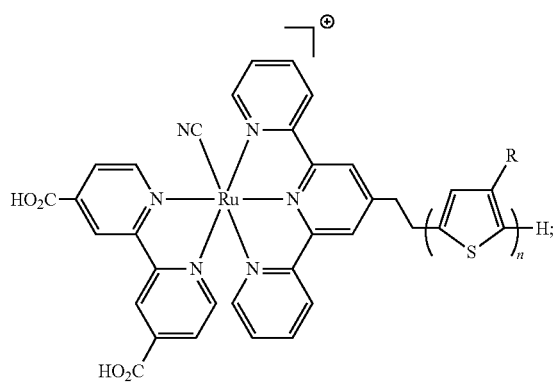

14

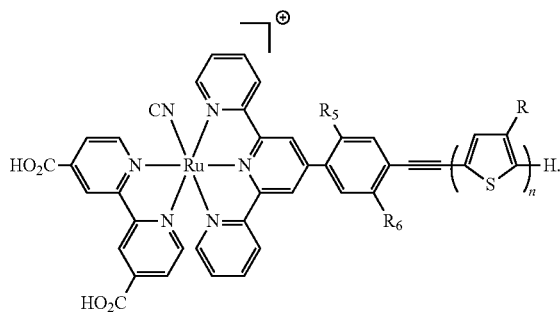

12. The process according to claim 11, in which the compound of formula 12 is prepared by reacting a compound of formula 10

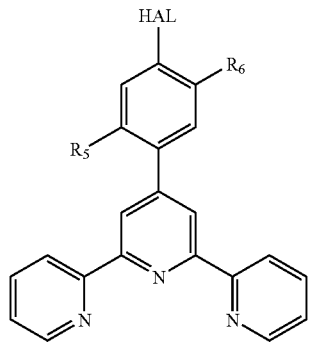

where HAL represents a halogen atom,
with a compound of formula 11

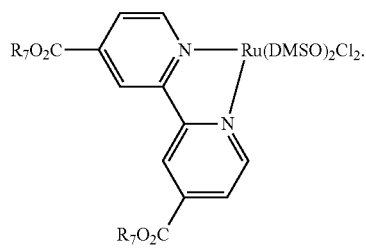

13. A pn-Semiconductive inorganic/organic hybrid material comprising a substrate of porous oxide ceramic to which a complex of formula (I), according to claim 1, is chemically grafted.

14. The material according to claim 13, in which the porous oxide ceramic is chosen from ceramics based on transition metals chosen from Ti, V, Cr, Mn, Fe, Co, Ni, Cu, Zn, Y, Zr, Nb, Mo, Ru, Rh, Pd, Ag, Cd, Hf, Ta, W, Re, Os, Ir, Pt, or based on lanthanides, such as La, Ce, Pr, Nd, Sm, Eu, Gd, Tb, Dy, Er, and Yb, or based on elements of group IIIA of the Periodic Table of Elements, chosen from Al, Ga, In and Tl, or based on elements of group IVA of the Periodic Table of Elements, chosen from Si, Ge, Sn and Pb, or based on elements of group VIA of the Periodic Table of Elements, chosen from Se and Te.

15. The material according to claim 13, in which the porous oxide ceramic is a mesoporous ceramic.

16. The material according to claim 15, in which the mesoporous ceramic is mesostructured.

17. The material according to claim 13, in which the ceramic is titanium dioxide $TiO_2$.

18. The process for preparing the semiconductive inorganic/organic hybrid material according to claim 13, in which a semiconductive porous oxide ceramic is impregnated with an organic solution containing one or more complexes of formula (I).

19. A photovoltaic cell comprising:
a current-collecting first electrode;
a second electrode; and
a semiconductive region consisting of a material as defined in claim 13, said region being placed between said first electrode and said second electrode.

20. The complex according to claim 4, wherein said sensitizing group S is selected from the group consisting of phthalocyanins, coumarins, and cyanins.

21. The complex according to claim 8, wherein n represents an integer from 5 to 100, and wherein R is selected from a group consisting of alkyl groups having from 4 to 12 carbon atoms, and alkoxy groups having from 4 to 12 carbon atoms.

22. The complex according to claim 8, wherein R is an n-octyl group.

23. The complex according to claim 9, wherein where $R_5$ and $R_6$ are selected from the group consisting of alkyl groups having from 1 to 12 carbon atoms, and alkoxy groups having from 1 to 12 carbon atoms, and wherein p is an integer from 1 to 4.

24. The complex according to claim 10, wherein n represents an integer from 5 to 100; R represents an alkyl group having from 4 to 12 carbon atoms, or an alkoxy group having from 4 to 12 carbon atoms; and $R_5$ and $R_6$ are selected from the group consisting of alkyl groups having from 1 to 12 carbon atoms, and alkoxy groups having from 1 to 12 carbon atoms.

* * * * *